United States Patent [19]

Ueda

[11] Patent Number: 4,808,505
[45] Date of Patent: Feb. 28, 1989

[54] PHOTOSENSITIVE MEMBER WITH ENAMINE CHARGE TRANSPORT MATERIAL

[75] Inventor: Hideaki Ueda, Kawanishi, Japan

[73] Assignee: Minolta Camera Kabushiki Kaisha, Osaka, Japan

[21] Appl. No.: 35,183

[22] Filed: Apr. 7, 1987

[30] Foreign Application Priority Data

| Apr. 8, 1986 | [JP] | Japan | 61-80780 |
| Apr. 16, 1986 | [JP] | Japan | 61-88491 |
| Apr. 16, 1986 | [JP] | Japan | 61-88492 |
| May 12, 1986 | [JP] | Japan | 61-108050 |
| May 12, 1986 | [JP] | Japan | 61-108052 |
| May 12, 1986 | [JP] | Japan | 61-108053 |
| May 20, 1986 | [JP] | Japan | 61-115916 |
| May 20, 1986 | [JP] | Japan | 61-115917 |
| May 20, 1986 | [JP] | Japan | 61-115918 |

[51] Int. Cl.$^4$ .............................. G03G 5/09
[52] U.S. Cl. .................................. 430/83; 430/59; 430/81; 430/95; 430/96
[58] Field of Search .................. 430/59, 81, 83, 90, 430/95

[56] References Cited

U.S. PATENT DOCUMENTS 4,334,001  6/1982  Horie et al. ................ 430/81 X

FOREIGN PATENT DOCUMENTS 48-28299  8/1973  Japan ........................... 430/83
59-165064  9/1984  Japan ........................... 430/59

Primary Examiner—Roland E. Martin
Attorney, Agent, or Firm—Burns, Doane, Swecker & Mathis

[57] ABSTRACT

The present invention relates to a photosensitive member, which comprises enamine compounds having a specific substituent on the nitrogen atom constituting the enamine bone, and has an excellent charge transportability.

16 Claims, 1 Drawing Sheet

PHOTOSENSITIVE MEMBER WITH ENAMINE CHARGE TRANSPORT MATERIAL

BACKGROUND OF THE INVENTION

In the electrophotographic art, the following methods are commonly known: the direct method, wherein the surface of a photosensitive layer of a photosensitive member is given a charge and subjected to an exposure to form a latent electrostatic image which is developed with a developer to visualize the image, thereupon the visualized image is directly fixed on the photosensitive member in order to provide a copied image; the toner image transfer method, wherein a visual image on a photosensitive member is transferred onto a transfer paper, e.g., paper where the transferred image is fixed to form a copied image; the latent image transfer method, wherein a latent electrostatic image on a photosensitive member is transferred onto a transfer paper where the latent electrostatic image is developed and fixed.

It is conventionally known that inorganic photoconductive materials, such as selenium, cadmium sulfate, zinc oxide and the like, are used as photoconductive materials to form the photosensitive layer of a photosensitive member employed in the electrophotographic methods, mentioned above. These photoconductive materials have diverse advantages; they can be given an electrical charge of a proper potential; the smaller effluence of charge in the dark, and the irradiation to light can rapidly neutralize the charge. Such materials, however, have various disadvantages. For example, selenium photosensitive materials incur greater manufacturing costs and require careful handling, since they are vulnerable to heat and mechanical impacts. Cadmium sulfate photosensitive members and zinc oxide photosensitive members cannot provide either stable sensitivity under the highly humid environment or stable properties for a longer period because a coloring material having been incorporated into the members causes both charge-oriented deterioration due to corona charge and colorfading due to exposure.

On the other hand, various organic photoconductive polymers including polyvinyl carbazole have been already proposed. Compared to the above-mentioned inorganic photoconductive materials, these polymers excel in the properties including coating properties, lightness, but are inferior in sensitivity, durability, and stability to environmental fluctuation.

Low molecule organic photoconductive compounds are preferable since their coating properties or electrophotograhic properties can be regulated by arbitrarily designating the type, composition and the like of a binder being used together with the compounds. However, the combined use with a binder requires that each of the compounds is highly compatible with the binder.

The photosensitive member containing high molecular or low molecular organic photoconductive compounds being dispersed into the resin of binder have disadvantages including a greater residual potential due to the greater traps in the carrier causes poor sensitivity. Accordingly, there have been proposals for blending a charge transporting material with an organic photoconductive compound in order to solve the above-mentioned disadvantages.

Diverse organic compounds have been disclosed as charge transporting materials, however, these compounds have various disadvantages. 2,5-bis(P-diethylaminophenyl)-1,3,4-oxadiazoles, for example, described in U.S. Pat. No. 3,189,447, have a poor compatibility with a binder, and tend to crystalize. Diarylalkane derivatives described in U.S. Pat. No. 3,820,989, though having satisfactory compatibility with a binder, develop deterioration in sensitivity due to repeated use. Hydrozon compounds described in Japanese Patent Publication Laid Open to Public Inspection No. 59143/1979, though having comparatively good residual potential properties, are disadvantageously inferior in sensitivity and charging capacity.

Thus, it is the fact that there are few charge transporting materials having properties practically advantageous in forming a photosensitive member.

SUMMARY OF THE INVENTION

The present invention provides a photosensitive member containing an enamine compound as a charge transporting material. The photosensitive member of the invention excels in the charge transporting properties, has a stable initial surface potential, and features a satisfactory charging capacity. With its charge transporting properties being remarkably excellent, and fewer traps in the carrier, a photosensitive member having much higher sensitivity than that obtainable from a conventional charge transporting material, can be provided.

BRIEF DESCRIPTION OF DRAWINGS

FIGS. 1, 4 and 5 respectively illustrate the structure of a dispersion type photosesitive member comprising an electroconductive substrate, provided thereon, a photosensitive layer.

FIGS. 2 and 3 respectively illustrate the structure of a function separating type photosensitive member comprising an electroconductive substrate, provided thereon, a charge generating layer and a charge transporting layer.

DETAILED DESCRIPTION OF THE INVENTION

Figure 1:
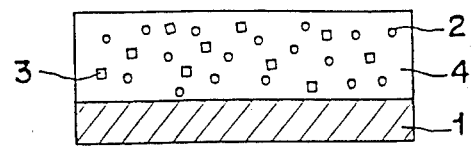
FIGS. 1 through 5 are schematic representations of photosensitive members according to the invention.

The present invention relates to a photosensitive member having a photosensitive layer containing an enamine compound represented by the general formula (I) as a charge transporting material:

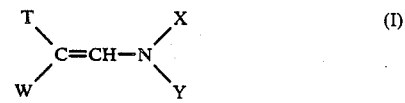

wherein, X and Y independently represents alkyl group, aryl group, aralkyl group, condensed polycyclic group or heterocyclic group, each of which may have a substituent, providing that at least one of X and Y is a condensed polycyclic group, heterocyclic group, alkyl aryl group or di-substituted aminoaryl group or a group represented by a formula:

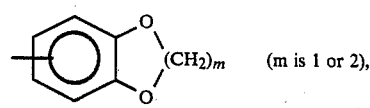

(m is 1 or 2), and T and W independently represent hydrogen, an alkyl group, aryl group, aralkyl group, condensed polycyclic group and heterocyclic group, each of which may have one or more substituent, except that the both T and W are not hydrogen.

A characteristic of the present invention is that the nitrogen atom constituting the enamine bone has at least one specific group X and/or Y, by which the enamine compounds give excellent charge transportability.

The specific group X and/or Y of the present invention is selected from the group consisting of a condensed polycyclic group, heterocyclic group, alkyl aryl group, di-substituted aminoaryl group or a group represented by a formula:

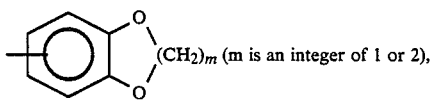

The condensed polycyclic group of the present invention is preferably naphthyl group, alkoxy naphthyl group, alkyl naphthyl group, di-substituted aminonaphthyl group, anthryl or fluorentyl group, which may have one or more substituents such as dioxaalkylene cyclic group, halogen, nitro group and the like. The condensed polycyclic group may have one or more substituents, for example, it may be trialkoxy naphthyl group.

The heterocyclic group of the present invention is preferably pyridyl group, pyrrolyl group, purinyl group, carbazolyl group, indolyl group, thienyl group, furyl group, quinolyl group, phenothiazinyl group, indolinyl group, tetrahydroquinolyl group, thiophenyl group, 2,3-dihydrobenzofuryl group, dihydrobenzopyryl group, benzothiazolyl group, benzooxazolyl group, benzoimidazolyl group, thiazolyl group or dibenzofuryl group. These heterocyclic groups may have one or more substituents such as alkyl group, halogen and the like.

The alkyl substituted aryl group of the present invention is an alkylphenyl group whose alkyl group has preferably a one to four carbon number atoms (referred to as $C_1$–$C_4$ alkyl group in this specification). The alkylphenyl group may have one or more different, or the same, alkyl groups, and other substituents such as halogen, alkoxy group and the like.

The di-substituted aminoaryl group of the present invention is preferably a phenyl group having a di-substituted amino group, which is selected from the group consisting of di($C_1$–$C_4$alkyl) amino group, morpholinyl group, piperidyl group, piperazinyl group, 2,3-dihydropyridyl group, tetrahydroquinolyl group, group. The di-substituted amino aryl group may have other substituents on the aryl group. Such as the substituent alkyl group, aryl group, alkoxy group and halogen.

The group represented by the formula:

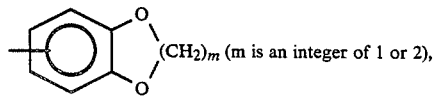

of the present invention may have one or more, the same or different substituents on the aryl group, the aryl group may be a condensed polycyclic group, such as naphthyl group, anthryl group, fluorenyl group and the like. The substituent may include alkyl group, aryl group, alkoxy group, halogen, and the like.

In the present invention the above specific group may be contained in the same enamine compound, for example, a compound having one alkylaryl group and one di-substituted aminoaryl group on the nitrogen atom of an enamine compound. One aryl group on the nitrogen may be aryl group having, for example, di-substituted amino group and alkoxy group, alkyl group and so on.

The T and W groups of the present invention are not restricted. However, a suitable group is an alkyl group aralkyl group, or aryl group, which may have one or more, of the same or different substituents such as alkyl, alkoxy, di-substituted amino, dioxaalkenyl, halogen and the like. An aryl group is most preferable, which may be phenyl group, naphthyl group, anthryl group, fluorenyl group and the like. The alkyl, alkoxy, and di-substituted amino group preferred as a substituent on the aryl group or aralkyl group, are $C_1$–$C_4$ alkyl, $C_1$–$C_4$ alkoxy, and $C_1$–$C_3$ alkyl di-substituted amino or cyclic amino.

The enamine compounds, according to the invention, represented by the general formula (I) are preferably those expressed by the following formulas (I-1)–(I-5). However, it should be noted that the scope of the invention is not limited only to these compounds.

One type of enamine compounds used in the invention are those expressed by the following general formula, (I-1);

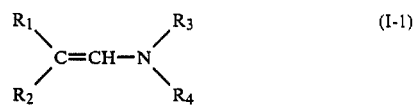

(wherein, $R_1$ represents any of a hydrogen atom, alkyl group, and aralkyl group; or an aryl group, condensed polycyclic group and heterocyclic group, each of which may have a substituent. $R_2$ represents any of an aryl group, condensed polycyclic group and heterocyclic group, each of which may have a substituent. $R_3$ represents any of a condensed polycyclic group and heterocyclic group, each of which may have a substituent. $R_4$ represents any of an alkyl group, aryl group, aralkyl group, condensed polycyclic group and heterocyclic group, each of which may have a substituent.)

As $R_3$ or $R_4$, an aryl group which may have a substituent is especially preferable. The preferred substituents are an alkyl group, alkoxy group, di-substituted amino group; a methoxy group, ethoxy group, methyl group, dimethylamino group and diethylamino group.

The preferred condensed polycyclic groups are a naphthyl group, anthryl group, pyrene group and the like, and may or may not have a substituent. The preferred substituents are an alkyl group and alkoxy group.

The preferred heterocyclic groups are a carbazolyl group, furyl group, thienyl group, phenothiazinyl group, indolyl group, indolinyl group, coumaranyl group, pyridinyl group, pyrrolyl group, benzimidazolyl group, thiazolyl group, benzothiazolyl group, benzoxazolyl group, phenazinyl group, phenoxazinyl group, oxazolyl group and oxadiazolyl group. These groups may or may not have a substituent.

The examples of such a substituent include an alkyl group, such as a methyl group, ethyl group, propyl group, methoxy group, ethoxy group and others.

Among the heterocyclic compounds, the preferred compounds having a nitrogen atom are those comprising a nitrogen atom, bonded thereon, any of the above-mentioned substituents.

When $R_5$ and $R_6$ comprise the groups described above, it is possible to obtain a photosensitive member having electrophotographic properties including the photosensitivity, residual potential, photo-fatigue, each of which is stable for a longer period. Especially, such a photosensitive member has a high photosensitivity and small residual potential.

The typical examples of the enamine compound expressed by the general formula (I-1) include those having the following structures.

(1-1)
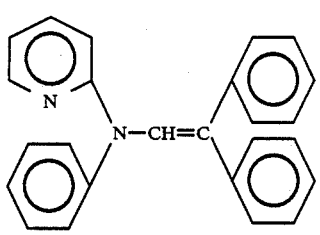

(1-2)
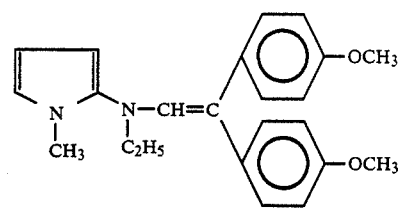

(1-3)
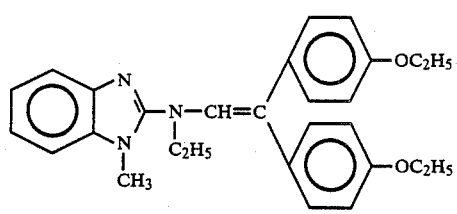

(1-4)
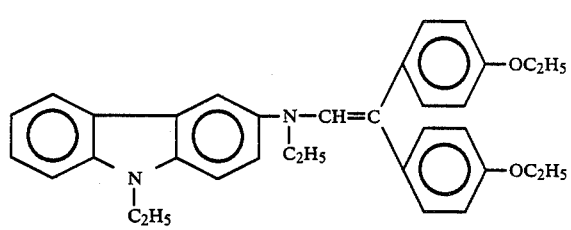

(1-5)
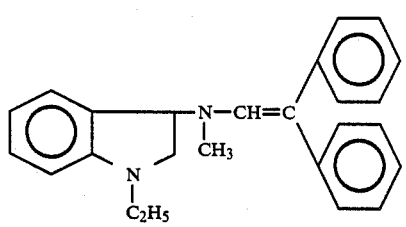

(1-6)
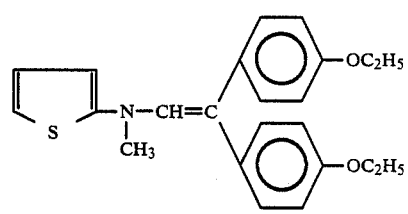

(1-7)
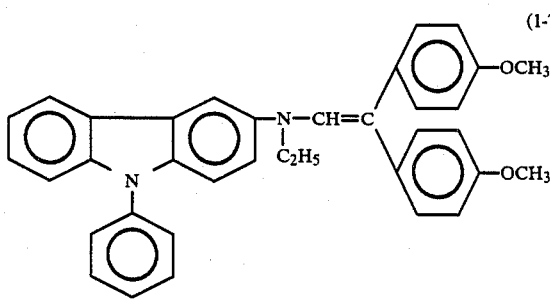

(1-8)
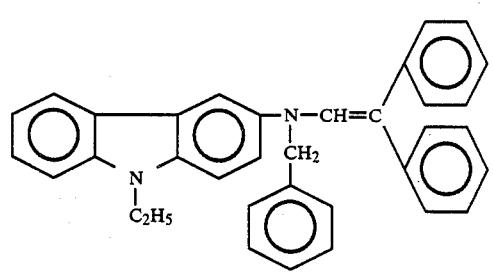

(1-9)
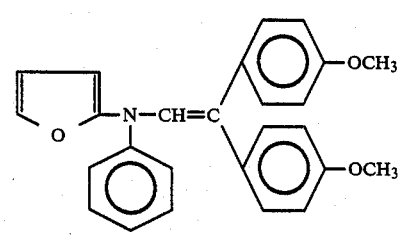

(1-11)
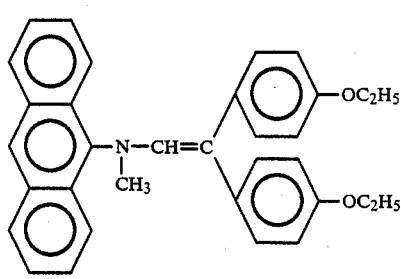

-continued
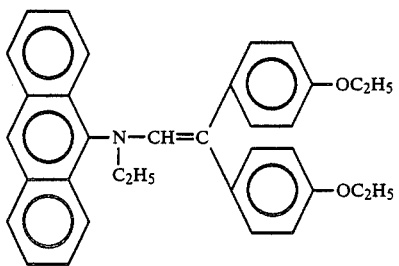 (1-12)
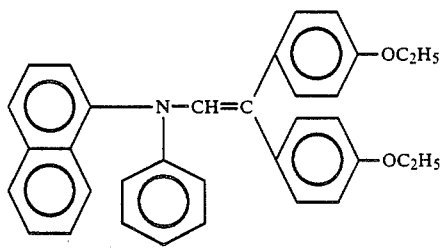 (1-13)
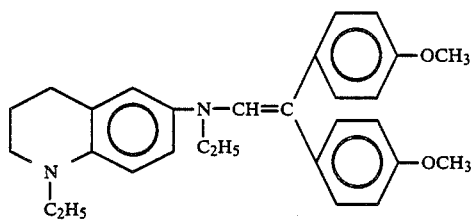 (1-14)
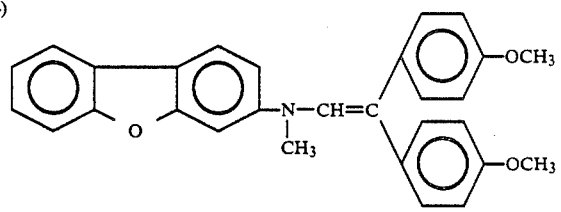 (1-15)
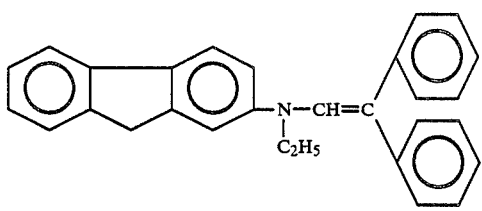 (1-16)
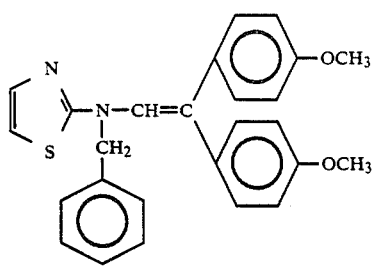 (1-17)
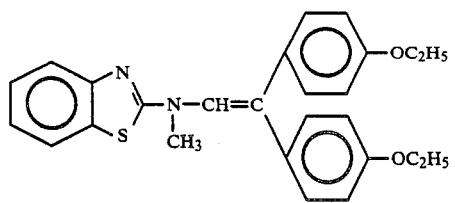 (1-18)
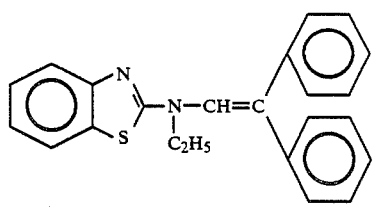 (1-19)
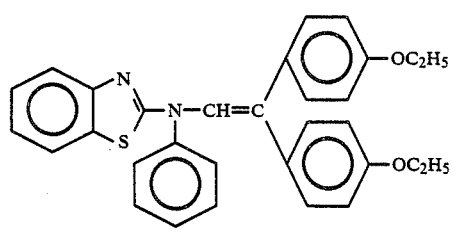 (1-20)
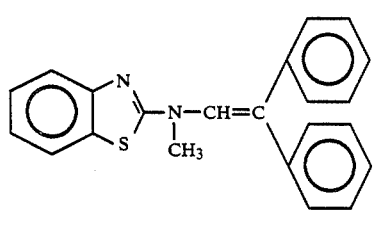 (1-21)
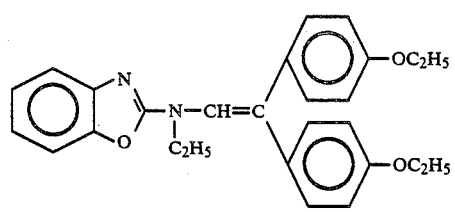 (1-22)
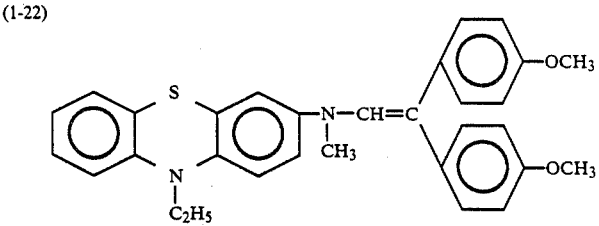 (1-23)

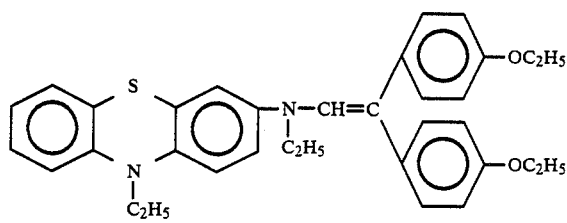 (1-24)

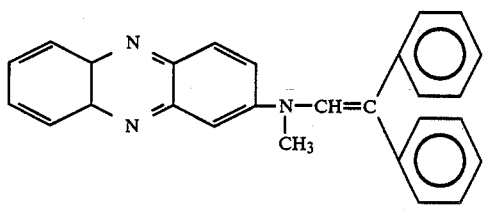 (1-25)

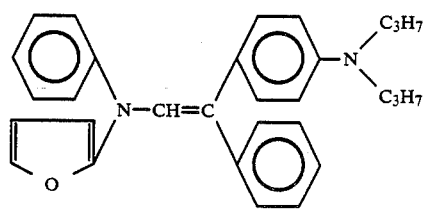 (1-26)

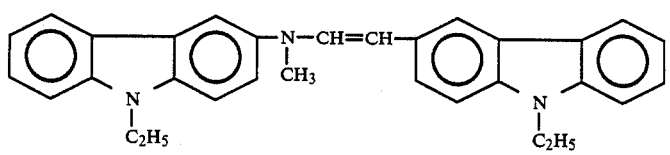 (1-27)

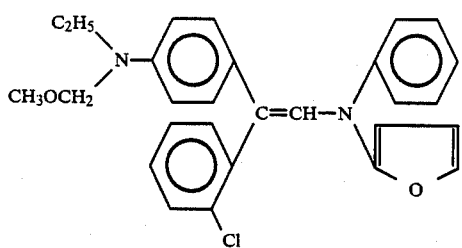 (1-29)

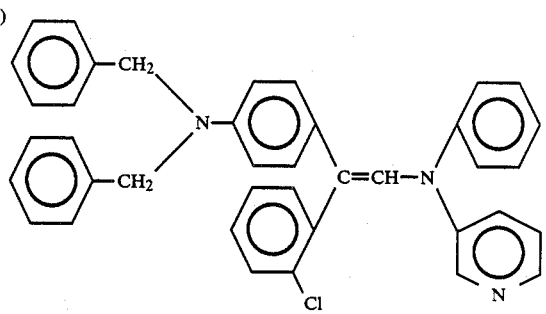 (1-30)

Other types of enamine compounds used in the invention are those expressed by the following general formula;

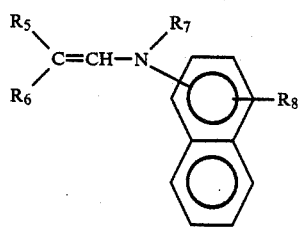 (I-2)

(wherein $R_5$ and $R_6$ independently represent hydrogen, aryl group or heterocyclic group, each of which may have a substituent ($R_5$ and $R_6$ cannot simultaneously be hydrogen atoms), $R_7$ represents an aryl group which may have a substituent, and $R_8$ represents hydrogen, alkyl group, alkoxy group or di-substituted amino group.)

The typical preferred enamine compounds, expressed by (I-2), include those having the following structures.

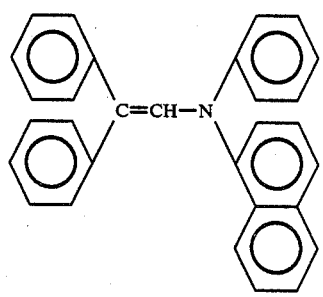 (2-1)

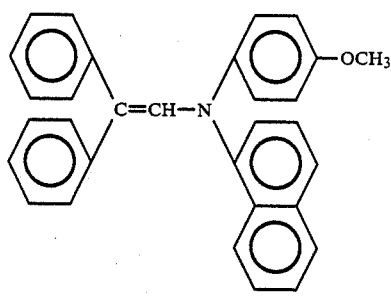 (2-2)

-continued
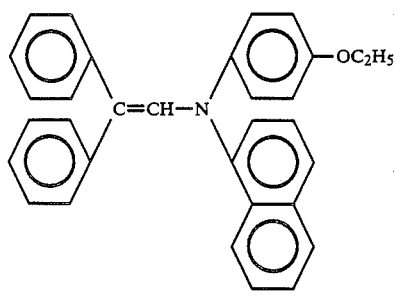
(2-3)
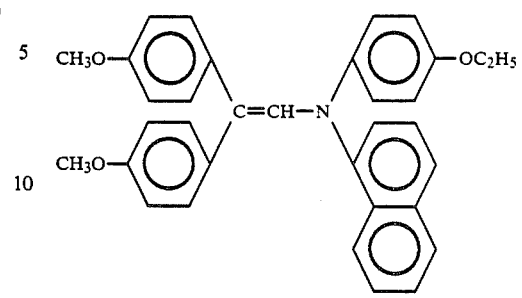
(2-8)
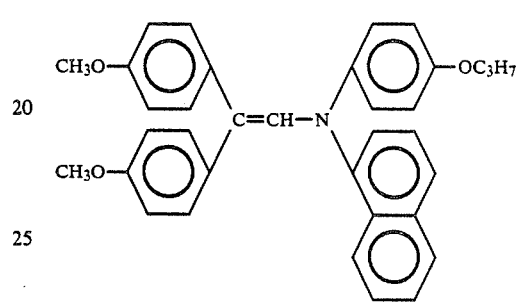
(2-9)
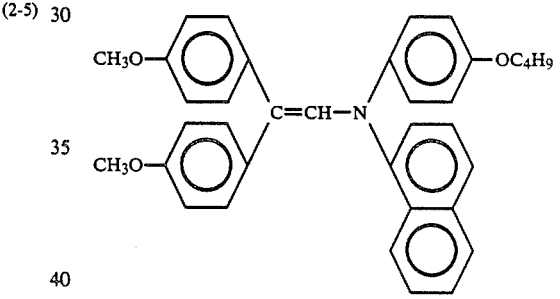
(2-10)
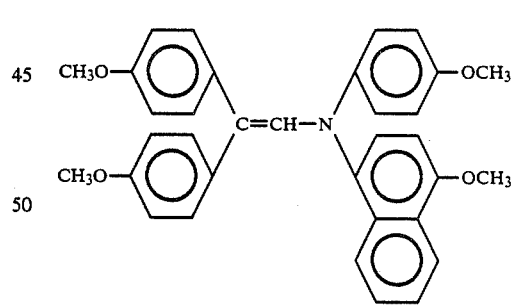
(2-11)
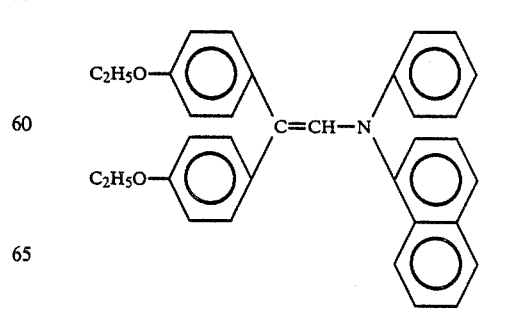
(2-12)

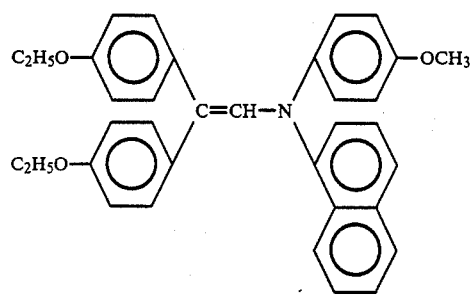
(2-13)
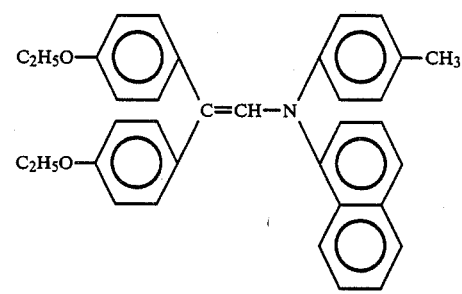
(2-14)
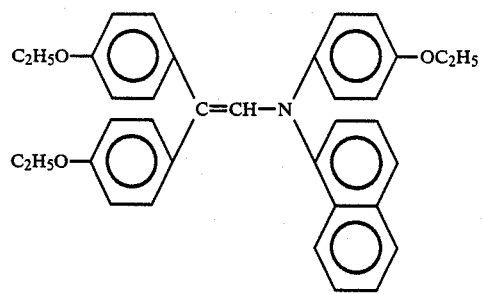
(2-15)
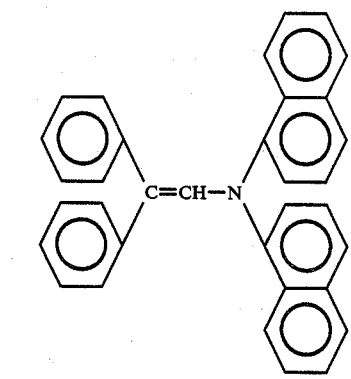
(2-16)
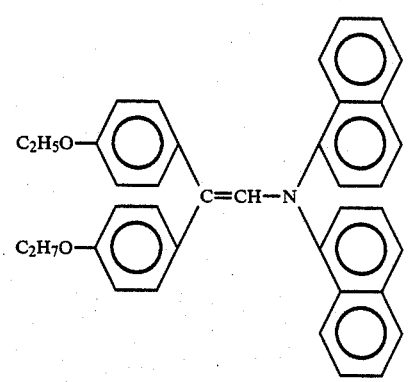
(2-17)
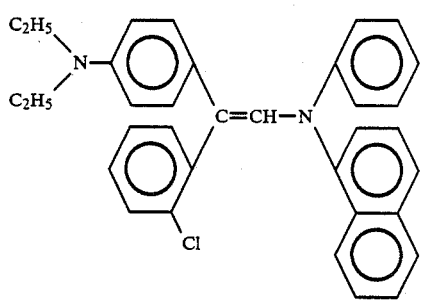
(2-18)
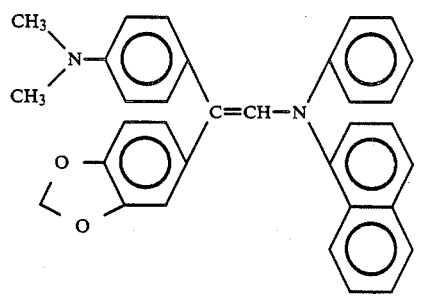
(2-19)
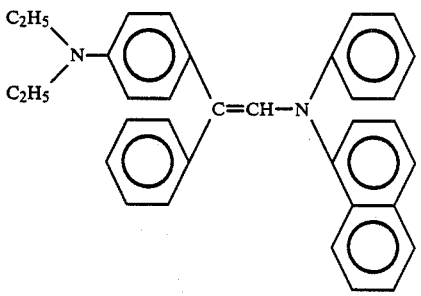
(2-20)
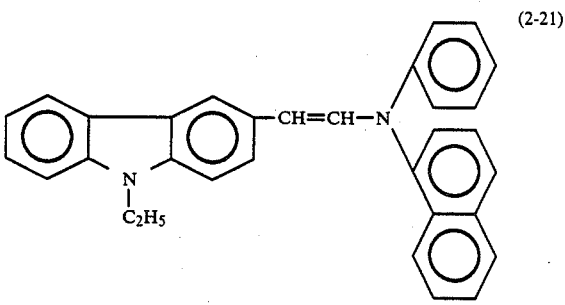
(2-21)
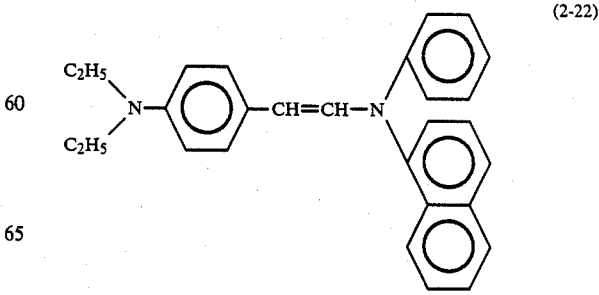
(2-22)

-continued
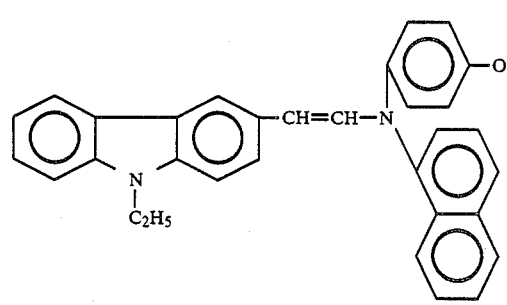 (2-23)
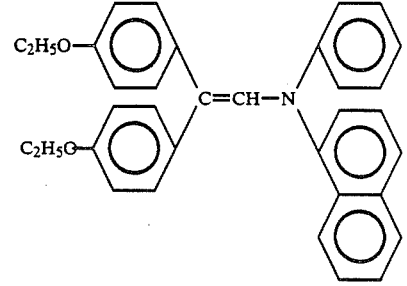 (2-28)
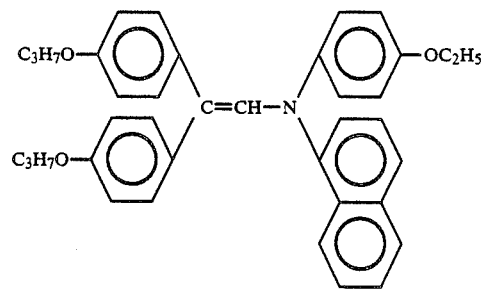 (2-24)
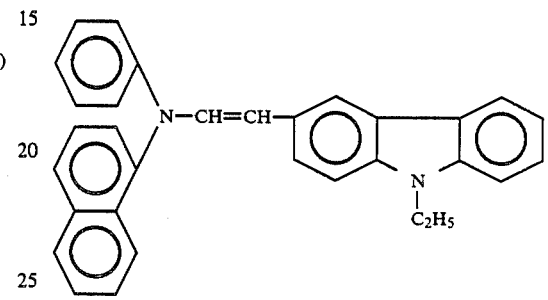 (2-29)
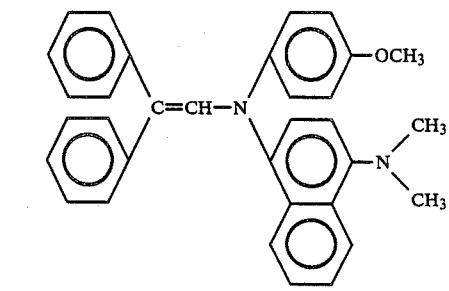 (2-25)
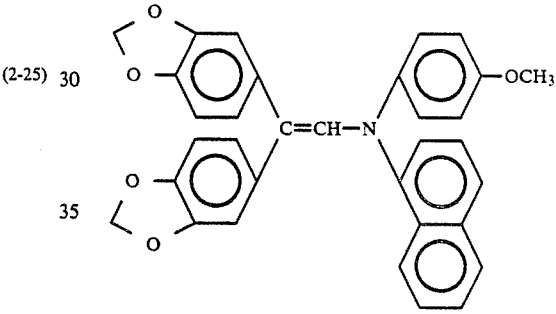 (2-30)
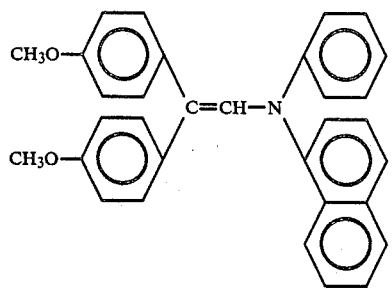 (2-26)
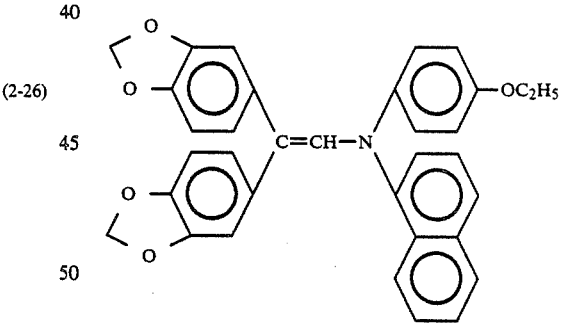 (2-31)
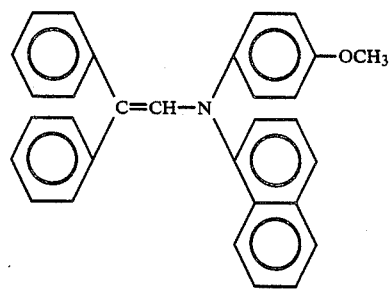 (2-27)
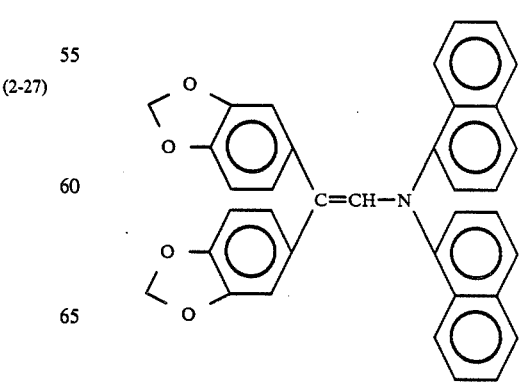 (2-32)

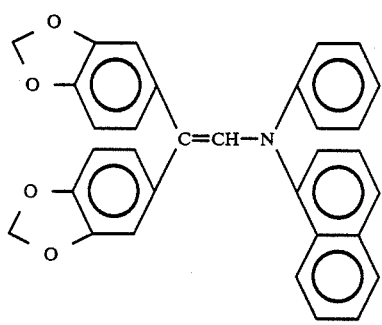 (2-33)
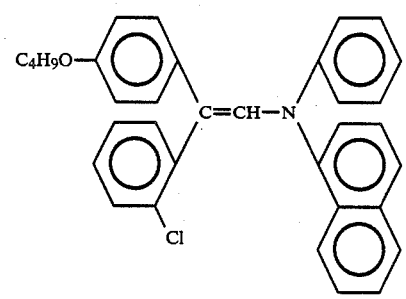 (2-34)
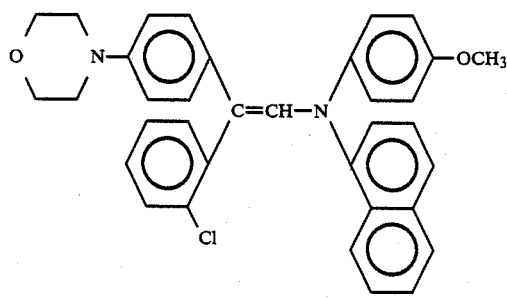 (2-35)
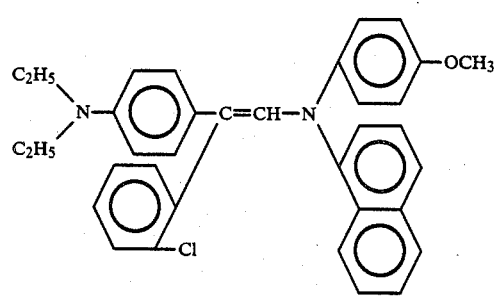 (2-36)
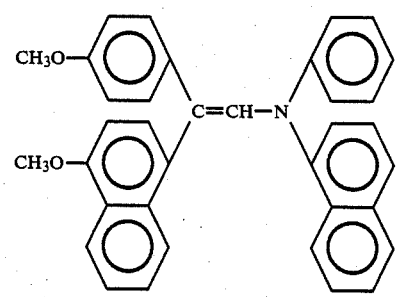 (2-37)
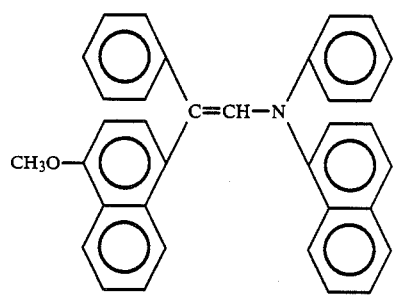 (2-38)
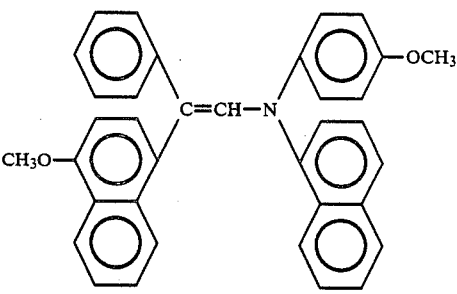 (2-39)
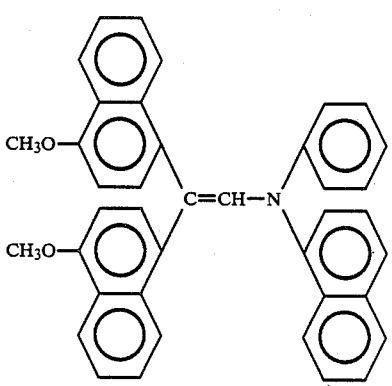 (2-40)
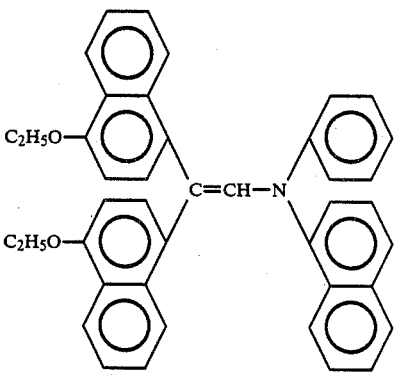 (2-41)
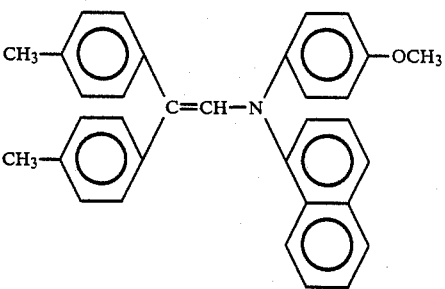 (2-42)

(2-43)

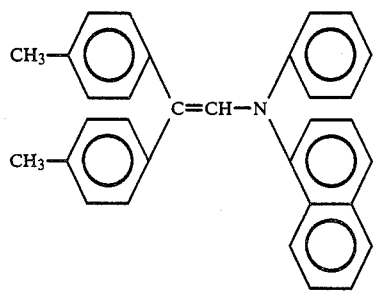

Still other enamine compounds used in the invention are those expressed by the following general formula:

(I-3)

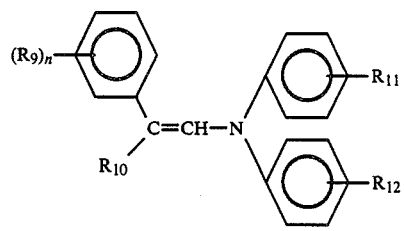

(wherein $R_9$ represents hydrogen, alkyl group, alkoxy group, phenoxy group, aralkyloxy group or di-substituted amino group, $R_{10}$ represents hydrogen, aryl group or heterocyclic group, each of which may have a substituent, $R_{11}$ represents an alkyl group, $R_{12}$ represents hydrogen, alkyl group, alkoxy group or di-substituted amino group, and n represents an integer of 1–3.)

The typical preferred enamine compounds, expressed by (I-3), include those having the following structures.

(3-1)

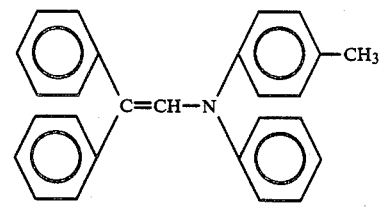

(3-2)

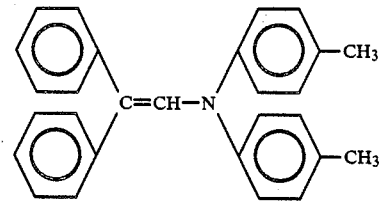

(3-3)

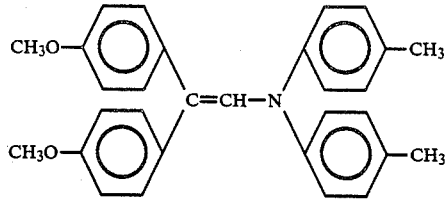

(3-4)

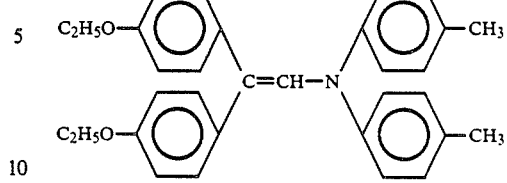

(3-5)

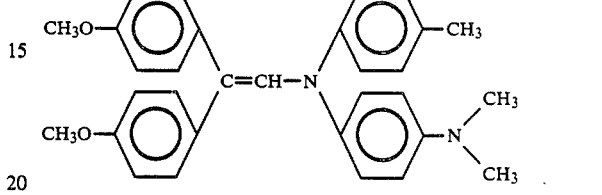

(3-6)

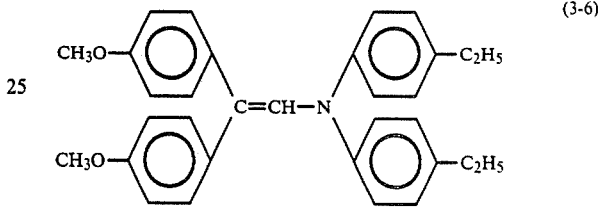

(3-7)

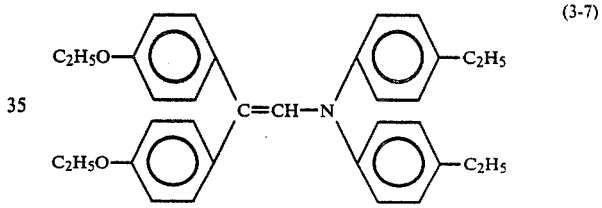

(3-8)

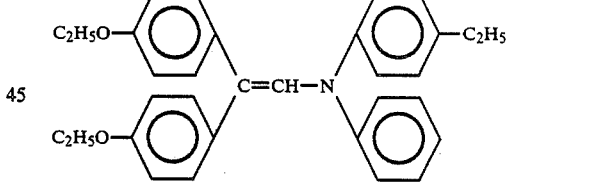

(3-9)

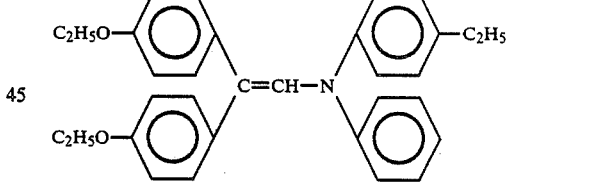

(3-10)

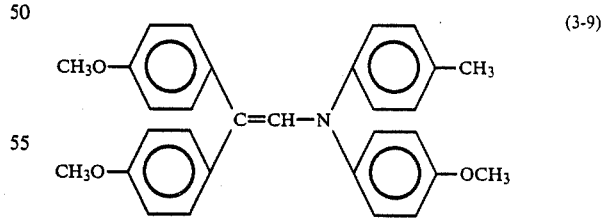

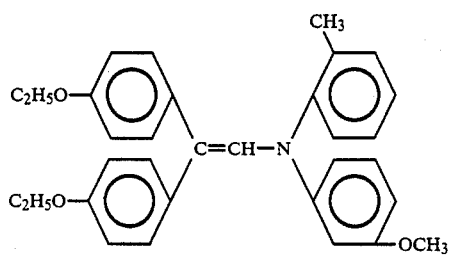 (3-11)
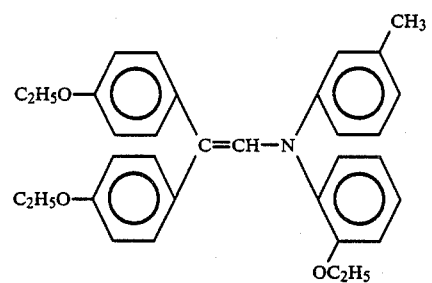 (3-12)
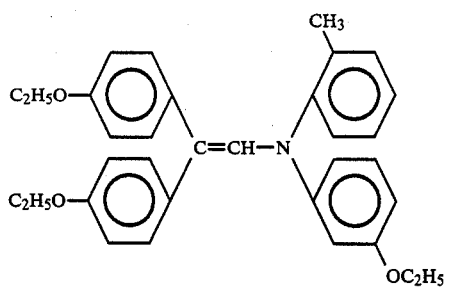 (3-13)
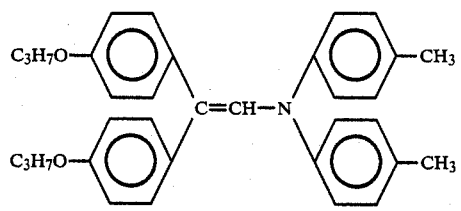 (3-14)
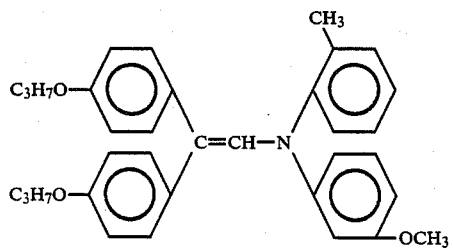 (3-15)
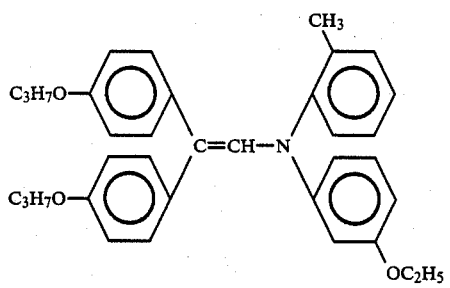 (3-16)
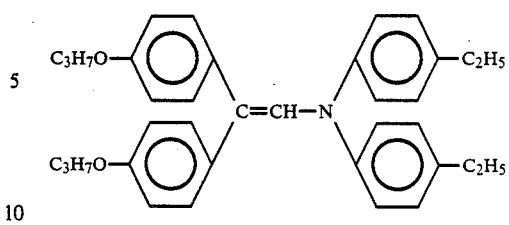 (3-17)
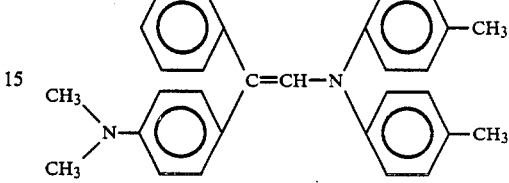 (3-18)
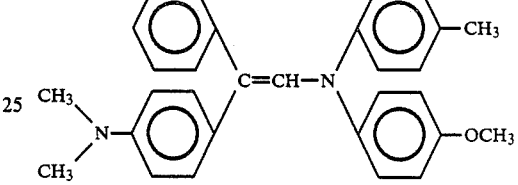 (3-19)
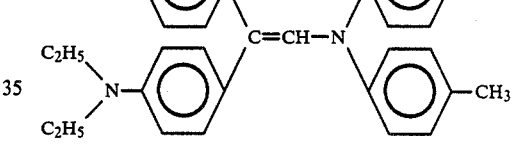 (3-20)
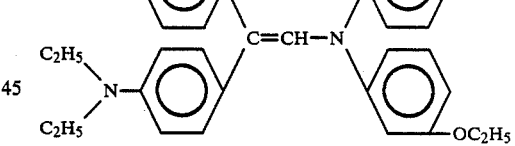 (3-21)
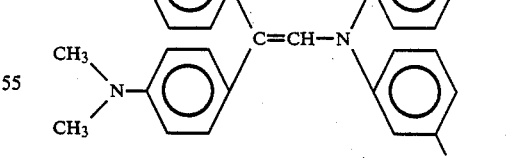 (3-22)
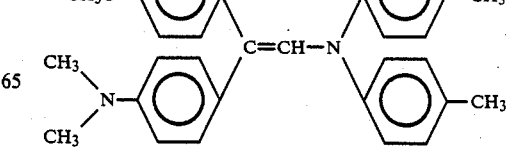 (3-23)

-continued
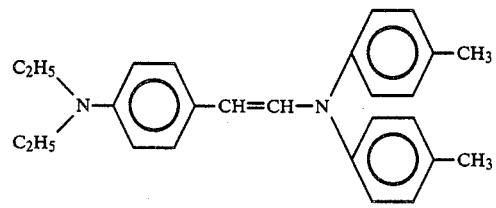 (3-24)
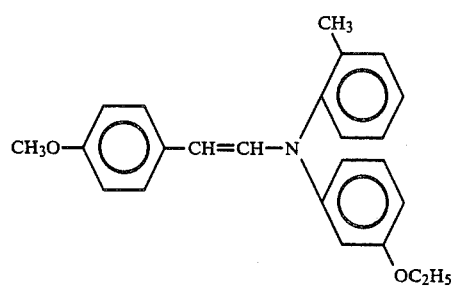 (3-25)
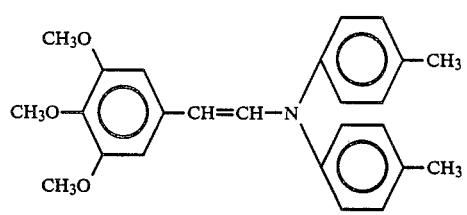 (3-26)
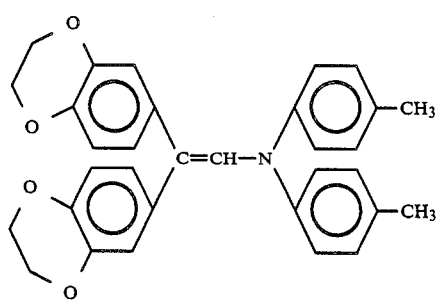 (3-27)
(3-28)
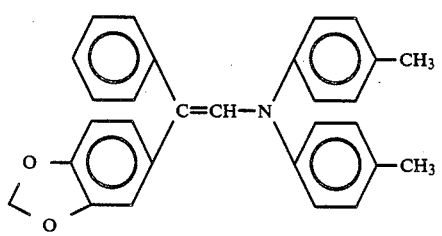 (3-29)
-continued
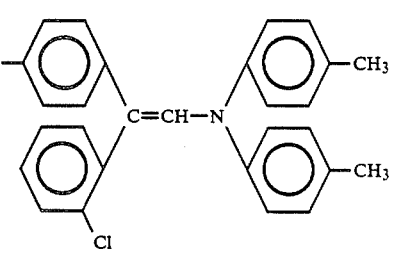 (3-30)
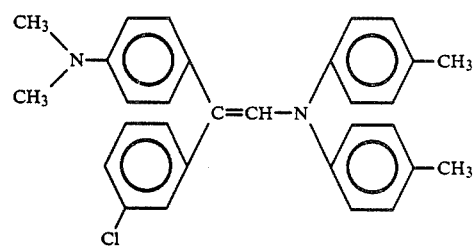 (3-31)
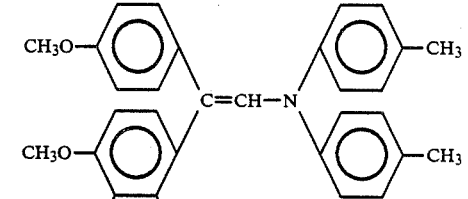 (3-32)
(3-33)
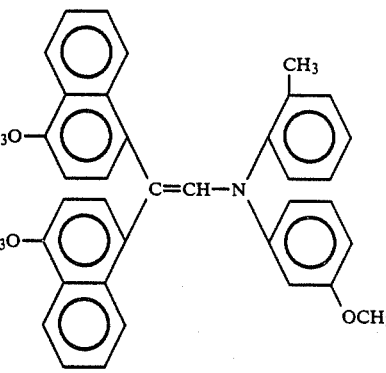 (3-34)
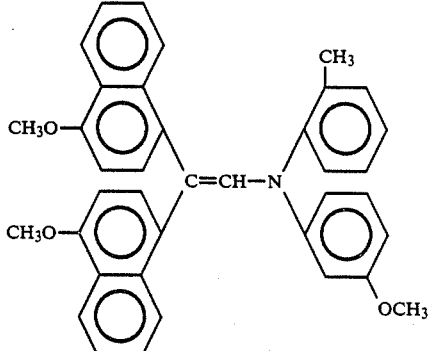

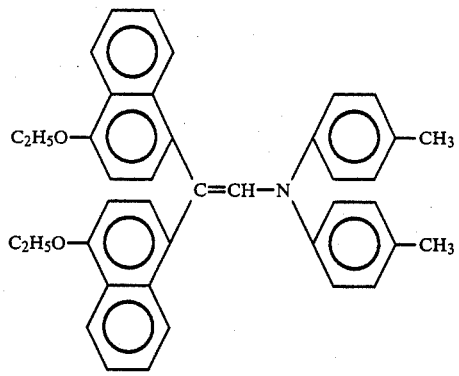
(3-35)

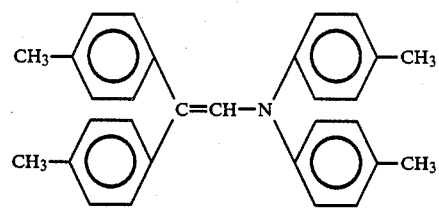
(3-36)

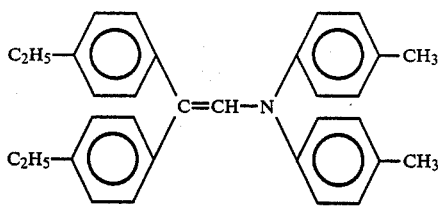
(3-37)

Still other enamine compounds used in the invention are those expressed by the following general formula

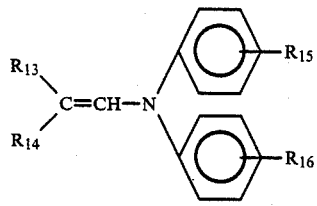
(I-4)

(wherein $R_{13}$ represents hydrogen, alkyl group or aryl group which may have a substituent, $R_{14}$ represents an aryl group or heterocyclic group, each of which may have a substituent, $R_{15}$ represents a di-substituted amino group, and $R_{16}$ represents hydrogen, alkyl group, alkoxy group, phenoxy group, aralkyloxy group or di-substituted amino group.)

The typical preferred enamine compounds, expressed by (I-4), include those having the following structural formulas.

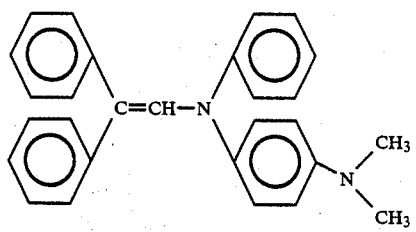
(4-1)

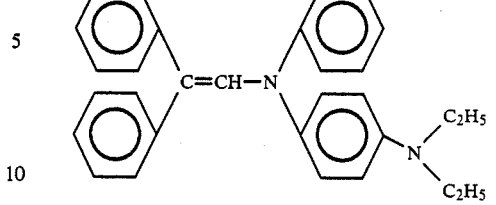
(4-2)

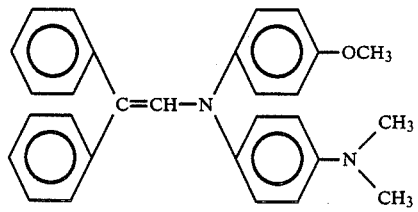
(4-3)

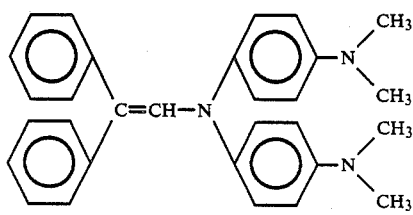
(4-4)

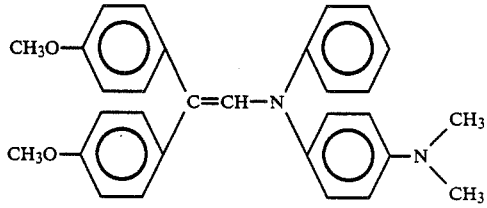
(4-5)

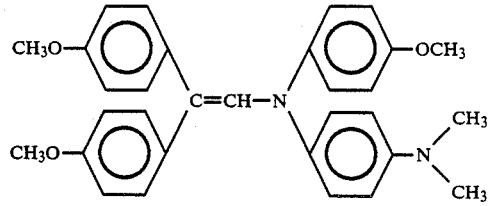
(4-6)

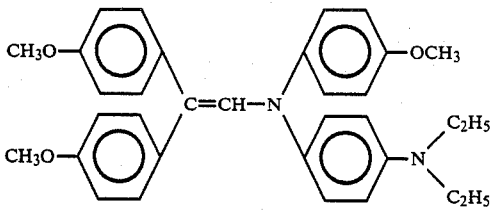
(4-7)

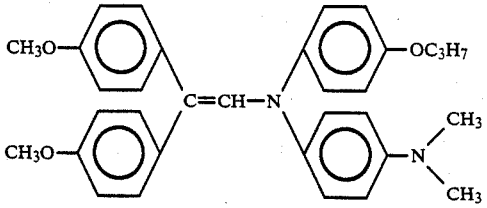
(4-8)

-continued
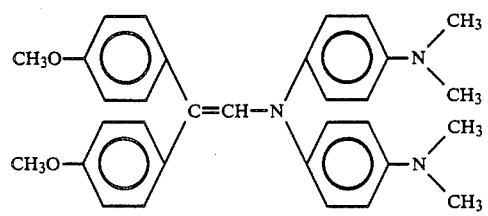 (4-9)
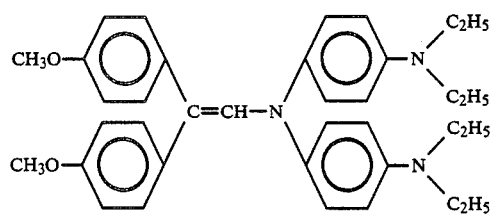 (4-10)
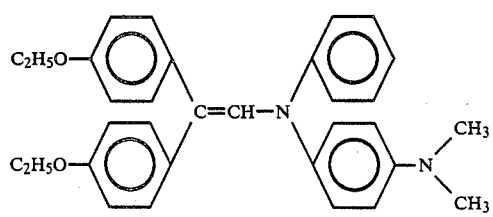 (4-11)
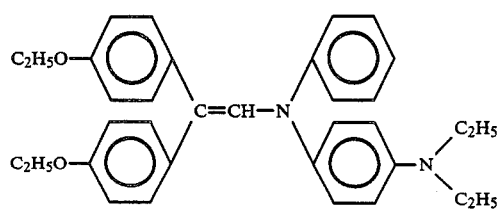 (4-12)
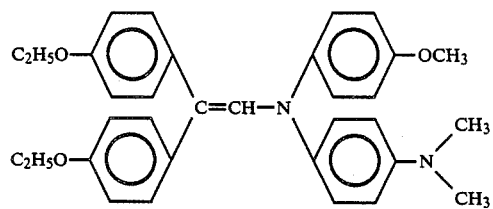 (4-13)
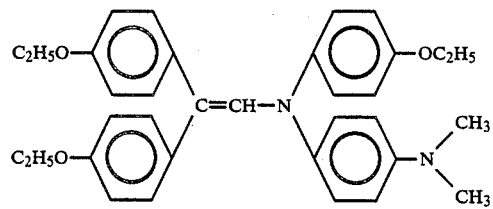 (4-14)
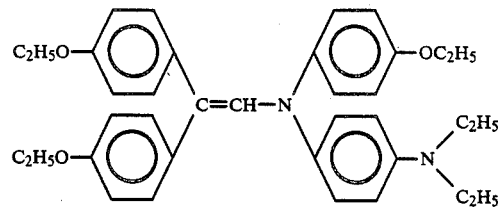 (4-15)
-continued
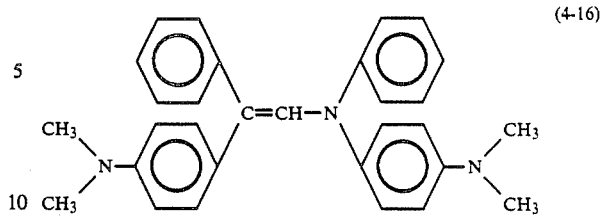 (4-16)
(4-17)
(4-18)
(4-19)
(4-20)
(4-21)

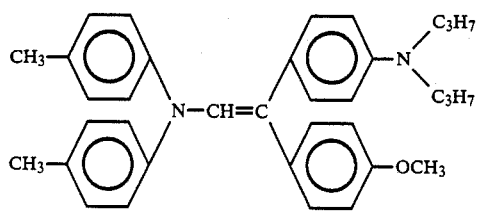
(4-22)

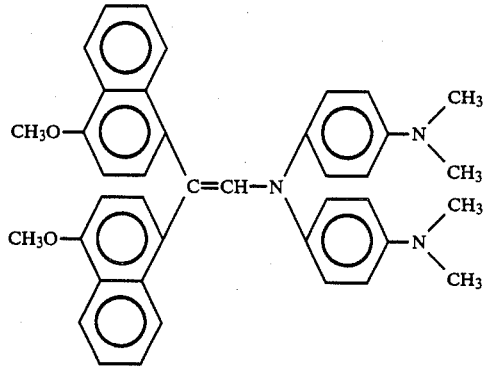
(4-23)

Still other enamine compounds in the present invention are those expressed by the following formula:

$$\begin{matrix} R_{17} \\ R_{18} \end{matrix} C=CH-N \begin{matrix} R_{19} \\ R_{20} \end{matrix}$$ (I-5)

(wherein $R_{17}$ represents hydrogen, alkyl group or aryl group which may have a substituent, $R_{18}$ represents an aryl group or heterocyclic group, each of which may have a substituent, $R_{19}$ represents a group represented by the formula:

$$Ar \underset{O}{\overset{O}{\diagup}} (CH_2)_m$$

(Ar is a phenyl group, naphthyl group, anthryl group or fluorenyl group; and m is 1 or 2), and $R_{20}$ represents hydrogen, alkyl group, alkoxy group, phenoxy group, aralkyloxy group, di-substituted amino group or a group represented by the formula:

[benzodioxole structure with $(CH_2)_m$]

and m is an integer of 1 or 2.

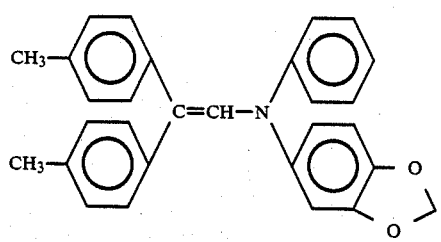
(5-1)

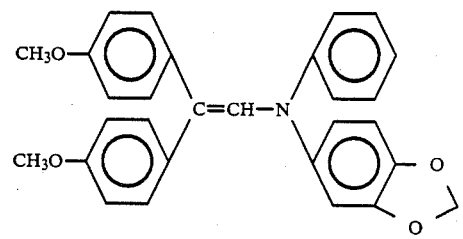
(5-2)

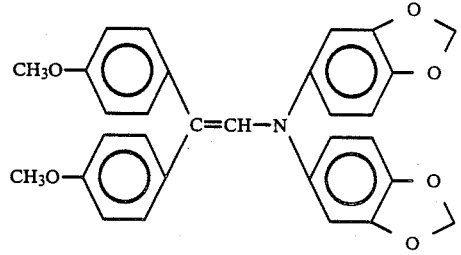
(5-3)

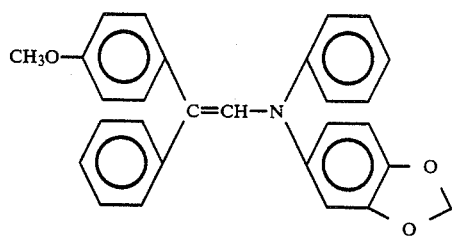
(5-4)

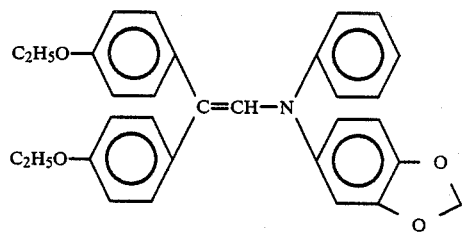
(5-5)

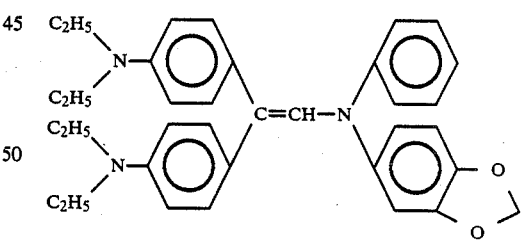
(5-6)

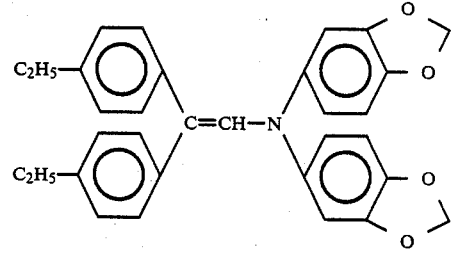
(5-7)

The enamine compounds expressed by the general formula (I) of the invention can be easily prepared with a known method.

For example, ordinary enamine compounds are synthesized with a method described in "Shin Jikken Kagaku Koza (lit., New Experimental Chemistry Course) 14-III, published by Maruzen Co., Ltd., pp 1417-1427.

The enamine compounds can be prepared by subjecting, for example, an amine compound expressed by the general formula (II),

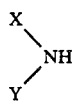
(II)

(wherein, X and Y are the same as those in (I)) and an aldehyde compound expressed by the general formula (II),

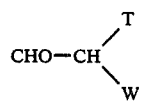
(III)

(wherein, T and W are the same as those in (I) to condensation via dehydration.

The condensation reaction is usually effected by removing the generated water through azeotropic distillation with a solvent such as benzene, toluene, xylene or the like, or by using a catalyst such as potassium carbonate, p-toluenesulfonic acid, acetic acid, Dowex 50 or Montmorillonite catalyst K10.

Desiccants used include molecular sieve, calcium oxide, calcium chloride, calcium carbonate and the like.

The constitutional examples of a photosensitive member using the enamine compound of the invention are schematically illustrated in FIGS. 1 through 5.

FIG. 1 illustrates a photosensitive member comprising a substrate 1, provided thereon, a photosensitive layer 4 containing a binder comprising a blend of a photoconductive material 3 and charge transporting material 2. As a charge transporting material, an enamine compound of the invention is used.

Figure 2:
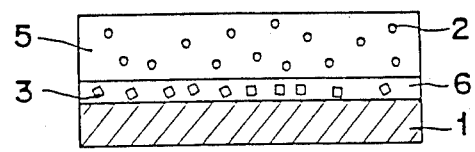

FIG. 2 illustrates a function-separating-type photosensitive member comprising, within a photosensitive layer, a charge generating layer 6 and a charge transporting member 5. The charge transporting layer 5 is provided on the surface of the charge generating layer 6. An enamine compound of the invention is blended into the charge transporting layer 5.

Figure 3:
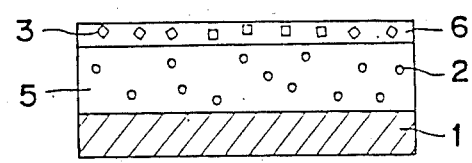

FIG. 3 illustrates a function-separating-type photosensitive member, similarly to FIG. 2, comprising both a charge generating layer 6 and a charge transporting layer 5. In contrast to FIG. 2, however, the charge generating layer is provided on the surface of the charge transporting layer 5.

Figure 4:
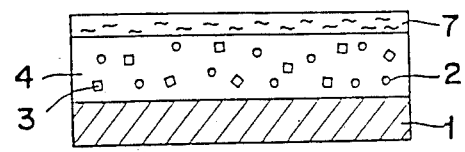

In FIG. 4, a surface protective layer 7 is additionally provided on the surface of the photosensitive member in FIG. 1, and a photosensitive layer 4 may be a function-separating-type layer comprising separately provided charge generating layer 6 and charge transporting layer 5.

Figure 5:
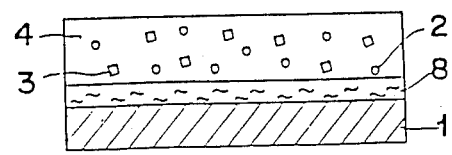

In FIG. 5, an intermediate layer 8 is provided between a substrate 1 and a photosensitive layer 4. Such an intermediate layer 8 can be provided in order to improve adhesion and coating properties, to protect the substrate, to improve the properties for injecting a charge from the substrate into the photoconductive layer. For an intermediate layer, a polyimide resin, polyester resin, polyvinylbutyral resin, casein and the like are advantageously used. A photosensitive member of this type may have a function separating type photosensitive layer.

The photosensitive member of the invention can be prepared by dissolving or dispersing an enamine compound expressed by the general formula (I) together with a binder into an optional appropriate solvent, into which a photoconductive material, electron attractive compound or sensitizing dye, and other pigments are further added in accordance with requirements; and the coating solution thus prepared is coated and dried on an electroconductive substrate so as to form a photosensitive layer having a thickness, normally 5-30 μm, preferably 6-20 μm.

More specifically, a function separating type photosensitive member having a constitution identical to that of FIG. 2 and comprising a charge generating layer and a charge transporting layer is prepared by forming a charge generating layer by vacuum-depositing a photoconductinve material on an electroconductive substrate, or by coating and drying, on an electroconductive substrate, a coating solution prepared by dispersing a photoconductive material into an optional appropriate solvent or solvent with a binder resin having been dissolved, and; by coating and drying, on the charge generating layer, a solution prepared by dissolving an enamine compound and a binder into an optional appropriate solvent, in order to form a charge transporting layer. The thickness of such a charge generating layer is less than 4 μm, and preferably less than 2 μm. The thickness of such a charge transporting layer is 3-30 μm, and preferably 5-20 μm. The advantageous content of enamine compound used in a charge transporting layer is 0.02-2 parts weight, or preferably 0.03-1.3 parts weight per part weight binder. Additionally, other charge transporting material may be combinedly employed. A high-polymer charge transporting material, which itself can be used as a binder, can avoids the use of other binder. A photosensitive member may, like the similar member in FIG. 3, have a constitution involving an electroconductive substrate, provided thereon, a charge transporting layer on which a charge generating layer is further disposed.

A dispersion type photosensitive member comprising an electroconductive substrate, provided thereon, a photosensitive layer and having a constitution identical with that in FIG. 1 is prepared by dispersing particles of a photoconductive material into a solution, into which an enamine compound and resin having been dissolved, and coating and drying the solution on an electroconductive substrate. The thickness of the photosensitive layer is 3-30 μm, or preferably 5-20 μm. Too small an amount of photoconductive material results in poor sensitivity. Too large an amount of the material results in poor charging properties and smaller mechanical strength of a photosensitive layer. Accordingly, the amount of photoconductive material within a photosensitive layer is 0.01-2 parts weight, or preferably 0.05-1 parts weight per part weight resin. The amount of enamine compound is 0.01-2 parts weight, or preferably 0.02-1.2 parts weight per part weight resin. Additionally, an enamine compound can be used combinedly with a high-molecular photoconductive material such as polyvinyl carbazole or the like which itself is usable as a binder. Also, an enamine compound can be used together with another charge transporting material such as a hydrazone compound.

Those used as a photoconductive material of a photosensitive member of the invention are as follows: organic materials such as a diazo pigment, triarylmethane dye, thiazine dye, oxazine dye, xanthene dye, cyanine coloring agent, styryl dye, pyrylium dye, azo pigment, quinachrydone dye, indigo pigment, perylene pigment, polycyclic quinone pigment, bisbenzimidazole pigment, indanthrone pigment, squalylium pigments and the like; and inorganic materials such as selenium, selenium-tellurium, selenium-arsenic, cadmium sulfide, amorphous silicon and the like. Other than these materials, any material may be used for this purpose, as far as it can absorb light and generate a highly efficient charged carrier.

As a binder used in the invention, any of the following can be used: electrically insulative and known thermoplastic resins; thermosetting resins and photosetting type resins and photoconductive resins.

Though not limiting the scope of the invention, the examples of appropriate binder resin are as follows; thermoplastic binders such as saturated polyester resin, polyamide resin, acryl resin, ethylenevinyl acetate copolymer, ion-bridged olefin copolymer (ionomer), styrene-butadiene block copolymer, polyallylate, polycarbonate, vinyl chloride-vinyl acetate copolymer, cellulose ester, polyimide, styrol resin and the like; thermosetting binders such as epoxy resin, urethane resin, silicon resin, phenol resin, melamine resin, xylene resin, alkyd resin, thermosetting acryl resin and the like; photosetting resins; photoconductive resins such as poly-N-vinylcarbazole, polyvinylpyrene, polyvinylanthracene and the like; and other resins. These resins may be used independently, or combinedly with the other resins.

Any of these electrically insulative resins has, when measured independently, a volume resistance greater than $1 \times 10^{12}$ Ω.cm. The more favorable resins are polyester resin, polycarbonate resin and acryl resin.

In addition to a binder, any of the following may be incorporated into a photosensitive member of the invention; plasticizers such as halogenated paraffin, polychlorinated biphenyl, dimethylnaphthalene, dibutylphthalate, O-terphenyl and the like; electron attractive sensitizers such as chloranil, tetracyanoethylene, 2,4,7-trinitro9-fluorenone, 5,6-dicyanobenzoquinone, tetracyanoquinodimethane, tetrachlorophthalic anhydride, 3,5-dinitrobenzoic acid and the like; sensitizers such as methyl violet, Rhodamine B, cyanine dye, pyrylium salt, thiapyrylium salt and the like.

A photosensitive member thus composed may have, as illustrated in FIGS. 4 and 5, an adhesive layer, intermediate layer 8 and surface protective layer 7, in accordance with specific requirements.

EXAMPLE 1

One part weight disazo pigment represented by the general formula (A), below, one part weight polyester resin (Vylon 200, manufactured by Toyobo Co., Ltd.) and 50 parts weight tetrahydrofuran were poured into a ball mill pot where they were blended for 24 hours to prepare a photosensitive coating solution. The solution was coated and dried on an aluminum substrate to form a charge generating layer with a thickness $0.5\mu$.

General formula:

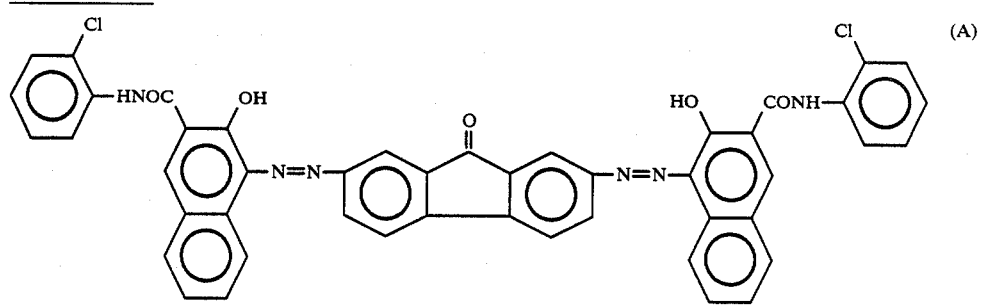

(A)

A coating solution prepared by dissolving ten parts weight of the previously mentioned enamine compound (1-1) and ten parts weight polycarbonate resin (Panlite K-1300, manufactured by Teijin Chemicals Ltd.) into 80 parts weight tetrahydrofuran was coated and dried on the charge generating layer to form a charge transporting layer with a thickness $15\mu$. Thus, a photosensitive member was prepared.

Using a commercial electrophotographic copier (EP360Z, manufactured by Minolta Camera Co., Ltd), the prepared photosensitive member was given a corona charge at $-6.0$ kV, then the initial potential V0(V), the exposure $E\frac{1}{2}$ (lux.sec) required to reduce the initial potential to $\frac{1}{2}$, and the reduction rate DDR5 (%) of the initial potential after the photosensitive member was left for five seconds in the dark were measured.

EXAMPLES 2–4

Using a method identical to that in Example 1, photosensitive members independently having the same constitution as Example 1 were prepared by using enamine compounds (1-3), (1-4) and (1-7) respectively in place of enamine compound (2-1) used in Example 1.

With each of the prepared photosensitive members, V0, $E\frac{1}{2}$ and DDR5 were measured by a method identical to that in Example 1.

EXAMPLE 5

Two parts weight trisazo pigment represented by the general formula (B), below, one part weight polyester resin (Vylon 200, manufactured by Toyobo Co., Ltd.) and 100 parts weight methyl ethyl ketone were poured into a ball mill pot, where they were dispersed for 24 hours to prepare a photosensitive coating liquid. The liquid was coated and dried on an aluminum substrate to form a charge generating layer with a thickness $1\mu$.

General formula:

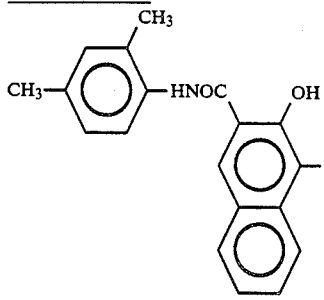
(B)

A coating solution prepared by dissolving 10 parts by weight of the previously mentioned enamine compound (1-9) and 10 parts by weight polyallylate resin (U-100, manufactured by Unitika Ltd.) into 100 parts weight chlorobenzene was coated and dried on the charge generating layer to form a charge transporting layer with a thickness of 15μ to give a photosensitive member.

With the prepared photosensitive member, V0, E½ and DDR5 were measured by a method identical to that in Example 1.

EXAMPLES 6-7

Electrophotographic photosensitive members were prepared in the same manner as Example 5, except that enamine compounds (1-11) and (1-13) were respectively used.

EXAMPLE 8

Two parts weight squalenic acid pigment represented by the general formula (C), below, five parts weight polyester resin (Vylon 200, manufactured by Toyobo Co., Ltd.) and 100 parts by weight methyl ethyl ketone were poured into a ball mill pot where they were blended for 24 hours to prepare a photosensitive coating solution. The solution was coated and dried on an aluminum substrate to form a charge generating layer with a thickness 1μ.

General formula:

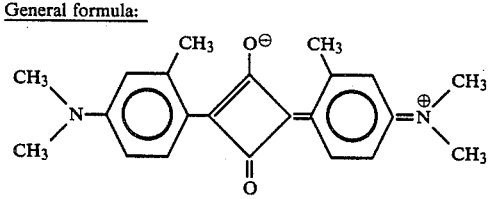
(C)

A coating solution, prepared by dissolving ten parts weight enamine compound (1-15) and ten parts by weight polycarbonate resin (Panlite, manufactured by Teijin Chemicals Ltd.) into 80 parts by weight tetrahydrofuran, was coated and dried on the charge generating layer to form a charge transporting layer with a thickness of 15μ when dried. Thus, a photosensitive member was prepared.

With the prepared photosensitive member, V0, E½ and DDR5 were measured with a method identical to that in Example 1.

EXAMPLE 9

Fifty parts by weight copper phthalocyanine and 0.2 parts by weight tetranitro copper phthalocyanine were, with through stirring, dissolved into 500 parts by weight of 98% concentrated sulfuric acid, which was poured into 5000 parts by weight water so as to precipitate a blend of photoconductive material comprising copper phthalocyanine and tetranitro copper phthalocyanine. Then, the precipitate was filtered off, washed with water, and dried at 120° C. under reduced pressure.

Ten parts by weight of the obtained photoconductive composition was poured into a ball mill pot together with 22.5 parts by weight thermosetting acryl resin (Acrydic A 405, manufactured by Dainippon Ink & Chemicals, Inc.), 7.5 weight parts melamine resin (Super Beckamine J820, manufactured by Dainippon Ink & Chemical, Inc.), ten parts by weight of the previously mentioned enamine compound (1-18), and 100 parts by weight mixed solvent comprising equal amount of methyl ethyl ketone and xylene. These were blended in a ball mill pot for 48 hours to prepare a photoconductive coating solution when was coated and dried on an aluminum substrate to form a photoconductive layer having a thickness of about 15μ. Thus a photosensitive member was prepared.

With the prepared photoconductive member, V0, E½ and DDR5 were measured with the method identical to that in Example 1, except that the member was given a corona charge at +6 KV.

EXAMPLES 10-12

Photosensitive members were prepared in the same manner as Example 9, except that enamine compounds (1-22), (1-23) and (1-24) were respectively used. To examine electrophotographic properties, the prepared electrophotographic photosensitive members were given a corona charge at −6.0 kV, for Examples 13-20, by using a commercial electrophotographic copier (EP360Z, manufactured by Minolta Camera Co., Ltd.). For Examples 11-12, the similar copier having been incorporated with a modification was used to give the members a corona charge at +6.0 kV in order to examine the similar properties.

With each member, an initial surface potential V0 (V), exposure E½ (lux.sec) required to reduce the initial potential to the half of it, and dark reduction rate DDR5 (%) of the initial potential after the member was left for five seconds in the dark were measured.

TABLE 1

|  | $V_0$ (V) | $E_{\frac{1}{2}}$ (lux · sec) | $DDR_1$ (%) |
|---|---|---|---|
| Example 1 | −670 | 3.8 | 3.5 |
| Example 2 | −660 | 3.0 | 4.0 |
| Example 3 | −650 | 2.6 | 7.0 |
| Example 4 | −660 | 2.5 | 5.0 |
| Example 5 | −660 | 5.8 | 4.5 |

TABLE 1-continued

|  | $V_0$ (V) | $E_{\frac{1}{2}}$ (lux · sec) | $DDR_1$ (%) |
| --- | --- | --- | --- |
| Example 6 | −670 | 5.1 | 3.0 |
| Example 7 | −650 | 3.0 | 8.0 |
| Example 8 | −650 | 6.2 | 9.0 |
| Example 9 | +640 | 2.6 | 11.0 |
| Example 10 | +640 | 2.2 | 11.5 |
| Example 11 | +630 | 2.2 | 12.0 |
| Example 12 | +650 | 2.3 | 10.0 |

EXAMPLE 13

An electrophotographic photosensitive member was prepared in the same manner as Example 1, except that enamine compound (2-2) was used instead of enamine compound (1-1).

Using a commercial electrophotographic copier (EP360Z, manufactured by Minolta Camera Co., Ltd), the obtained photosensitive member was given a corona charge at −6.0 kV, then the initial potential V0 (V), the exposure $E_{\frac{1}{2}}$ (lux.sec) required to reduce the initial potential to $\frac{1}{2}$, and the reduction rate DDR5 (%) of the initial potential after the photosensitive member was left for five seconds in the dark were measured.

EXAMPLES 14-16

Using a method identical to that in Example 13, photosensitive members independently having the same constitution as Example 13 were prepared by using enamine compounds (2-3), (2-5) and (2-6) respectively in place of enamine compound (2-2) used in Example 13.

With each of the prepared photosensitive members, V0, $E_{\frac{1}{2}}$ and DDR5 were measured by a method identical to that in Example 13.

EXAMPLE 17

Two parts by weight trisazo pigment represented by the general formula (B), one part by weight polyester resin (Vylon 200, manufactured by Toyobo Co., Ltd.) and 100 parts by weight methyl ethyl ketone were poured into a ball mill pot, where they were blended for 24 hours to prepare a photosensitive coating solution. The solution was coated and dried on an aluminum substrated to form a charge generating layer with a thickness of 1μ.

A coating solution prepared by dissolving ten parts by weight of the previously mentioned enamine compound (2-7) and ten parts by weight polyallylate resin (U-100, manufactured by Unitika Ltd.) into 100 parts by weight chlorobenzene was coated and dried on the charge generating layer to form a charge transporting layer with a thickness of 15μ. Thus, a photosensitive member was prepared.

With the prepared photosensitive member, V0, $E_{\frac{1}{2}}$ and DDR5 were measured by a method identical to that in Example 13.

EXAMPLES 18-19

Using a method identical to that in Example 17, photosensitive members independently having the same constitution as Example 17 were prepared by using enamine compounds (2-8) and (2-9) respectively in place of enamine compound (2-7) used in Example 17.

With each of the prepared photosensitive members, V0, $E_{\frac{1}{2}}$ and DDR5 were measured by a method identical to that in Example 1.

EXAMPLE 20

An electrophotographic photosensitive member was prepared in the same manner as Example 8, except that enamine compound (2-12) was used instead of enamine compound (1-15).

With each of the prepared photosensitive members, V0, $E_{\frac{1}{2}}$ and DDR5 were measured by a method identical to that in Example 1.

EXAMPLE 21

An electrophotographic photosensitive member was prepared in the same manner as Example 9, except that enamine compound (2-13) was used instead of enamine compound (1-18).

With the prepared photosensitive member, V0, $E_{\frac{1}{2}}$ and DDR5 were measured with the method identical to that in Example 9, except that the member was given a corona charge at +6 kV.

EXAMPLES 22-24

Using a method identical to that in Example 21, photosensitive members independently having the same constitution as Example 21 were prepared by using enamine compounds (2-15), (2-19) and (2-20) respectively in place of enamine compound (2-13) used in Example 21.

With each of the prepared photosensitive members, V0, $E_{\frac{1}{2}}$ and DDR5 were measured by a method identical to that in Example 9.

The measuring results of V0, $E_{\frac{1}{2}}$ and DDR5 for photosensitive members of Examples 13-24 are shown in Table 2.

TABLE 2

|  | $V_0$ (V) | $E_{\frac{1}{2}}$ (lux · sec) | $DDR_5$ (%) |
| --- | --- | --- | --- |
| Example 13 | −660 | 2.7 | 6.0 |
| Example 14 | −650 | 2.5 | 7.0 |
| Example 15 | −670 | 2.2 | 6.0 |
| Example 16 | −660 | 2.3 | 5.5 |
| Example 17 | −660 | 2.4 | 6.0 |
| Example 18 | −650 | 2.1 | 6.5 |
| Example 19 | −660 | 2.0 | 6.5 |
| Example 20 | −650 | 3.8 | 7.0 |
| Example 21 | +630 | 2.0 | 12.0 |
| Example 22 | +640 | 1.8 | 11.0 |
| Example 23 | +650 | 2.2 | 10.5 |
| Example 24 | +640 | 1.7 | 12.0 |

As can be understood from Table 2, every photosensitive member of the invention has a stable initial surface potential of more than 600 V, and excellent charging properties as its dark reduction rate is small enough for the practical use of a photosensitive member. The table also shows that every photosensitive member of the invention has a stable and high sensitivity.

EXAMPLE 25

One part weight E type copper phthalocyanine (manufactured by Toyo Ink Mfg. Co., Ltd.), one part by weight polyester resin (Vylon 200, manufactured by Toyobo Co., Ltd.) and 50 parts by weight tetrahydrofuran were poured into a ball mill pot where they were blended for 24 hours to prepare a photosensitive coating solution. The solution was coated and dried on an aluminum substrate to form a charge generating layer having a thickness of 1μ.

A coating solution prepared by dissolving ten parts weight of the previously mentioned enamine compound (3-3) and ten parts by weight polycarbonate resin (Panlite K-1300, manufactured by Teijin Chemicals Ltd.) into 100 parts by weight tetrahydrofuran was coated and dried on the charge generating layer to form a charge transporting layer with a thickness of 15μ. Thus, a photosensitive member was prepared.

Using a commercial electrophotographic copier (EP450Z, manufactured by Minolta Camera Co., Ltd), the prepared photosensitive member was given a corona charge at 6 kV, then the initial potential $V_0(V)$, the exposure $E_{\frac{1}{2}}$ (lux.sec) required to reduce the initial potential to $\frac{1}{2}$, and the reduction rate $DDR_5$ (%) of the initial potential after the photosensitive member was left for five seconds in the dark were measured.

EXAMPLES 26–28

Using a method identical to that in Example 25, photosensitive members independently having the same constitution as Example 25 were prepared by using enamine compounds (3-4), (3-5) and (3-11) respectively in place of enamine compound (3-3) used in Example 25.

With each of the prepared photosensitive members, $V_0$, $E_{\frac{1}{2}}$ and $DDR_5$ were measured by a method identical to that in Example 25.

EXAMPLE 29

Fifty parts weight copper phthalocyanine and 0.2 parts by weight tetranitro copper phthalocyanine were, with thorough stirring, dissolved into 500 parts by weight of 98% concentrated sulfuric acid, which was poured into 5000 parts by weight water so as to precipitate a blend of a photoconductive material comprising copper phthalocyanine and tetranitro copper phthalocyanine. Then, the precipitate was filtered, washed with water, and dried at 120° C. under reduced pressure.

Ten parts weight of the obtained photoconductive composition was poured into a ball mill pot together with 22.5 parts by weight thermosetting acryl resin (Acrydic A 405, manufactured by Dainippon Ink & Chemicals, Inc.), 7.5 weight parts melamine resin (Super Beckamine J820, manufactured by Dainippon Ink & Chemical, Inc.), ten parts by weight of the previously mentioned enamine compound (3-11), and 100 parts by weight mixed solvent comprising equal amounts of methyl ethyl ketone and xylene. They were blended in a ball mill pot for 48 hours to prepare a photoconductive coating solution, which was coated and dried on an aluminum substrate to form a photosensitive layer having a thickness about 15μ. Thus a photosensitive member was prepared.

With the prepared photosensitive member, $V_0$, $E_{\frac{1}{2}}$ and $DDR_5$ were measured with the method identical to that in Example 68, except that the member was given corona charge at +6 kV.

EXAMPLES 30–32

Using a method identical to that in Example 29, photosensitive members independently having the same constitution as Example 29 were prepared by using enamine compounds (3-12), (3-13) and (3-14) respectively in place of enamine compound (3-11) used in Example 29.

With each of the prepared photosensitive members, $V_0$, $E_{\frac{1}{2}}$ and $DDR_5$ were measured by a method identical to that in Example 29.

EXAMPLE 33

Two parts by weight disazo pigment represented by the general formula (A), below, one part weight polyester resin (Vylon 200, manufactured by Toyobo Co., Ltd.) and 100 parts by weight methyl ethyl ketone were poured into a ball mill pot where they were blended for 24 hours to prepare a photosensitive coating solution. The solution was coated and dried on an aluminum substrate to form a charge generating layer with a thickness of 1μ.

A coating solution prepared by dissolving ten parts weight of the previously mentioned enamine compound (3-18) into solvent, comprising polyallylate resin (U-100, manufactured by Unitika Ltd.) and 100 parts by weight chlorobenzene, was coated and dried on the charge generating layer to form a charge transporting layer with a thickness of 15. Thus, a photosensitive member was prepared.

WIth the prepared photosensitive member, $V_0$, $E_{\frac{1}{2}}$ and $DDR_5$ were measured by a method identical to that in Example 25.

EXAMPLES 34–35

Using a method identical to that in Example 33, photosensitive members independently having the same constitution as Example 33 were prepared by using enamine compounds (3-20) and (3-21) respectively in place of enamine compound (3-18) used in Example 33.

With each of the prepared photosensitive members, $V_0$, $E_{\frac{1}{2}}$ and $DDR_5$ were measured by a method identical to that in Example 25.

The measurement results of $V_0$, $E_{\frac{1}{2}}$ and $DDR_5$ for photosensitive members of Examples 25–35 are shown in Table 3.

TABLE 3

| | $V_0$ | $E_{\frac{1}{2}}$ (lux · sec) | $DDR_5$ (%) |
|---|---|---|---|
| Example 25 | −670 | 3.2 | 4.0 |
| Example 26 | −680 | 3.0 | 3.0 |
| Example 27 | −670 | 2.8 | 4.5 |
| Example 28 | −680 | 2.9 | 3.0 |
| Example 29 | +640 | 2.3 | 12.0 |
| Example 30 | +650 | 2.0 | 10.0 |
| Example 31 | +640 | 1.9 | 11.0 |
| Example 32 | +630 | 2.0 | 13.0 |
| Example 33 | −660 | 2.1 | 5.0 |
| Example 34 | −670 | 1.8 | 3.0 |
| Example 35 | −660 | 2.0 | 4.0 |

As can be understood from Table 3, every photosensitive member of the invention has a stable initial surface potential of more than 600 V, and excellent charging properties as its dark reduction rate is small enough for the practical use of a photosensitive member. The table also shows that every photosensitive member of the invention has a smaller $E_{\frac{1}{2}}$ and high sensitivity. Furthermore, using an electrophotographic copier (EP350Z, manufactured by Minolta Camera Co., Ltd.), the copying operation was repeated by giving a positive charge to the photosensitive members, Examples 29 and 30. In 10,000 copying sequences, both the first and final dequences could provide a copied image having excellent gradation. Without any change in sensitivity, high-definition images were obtained throughout the 10,000 copying sequences. Thus, every photosensitive member of the invention has stable repeatability.

EXAMPLE 36

An electrophotographic photosensitive member was prepared in the same manner as Example 25, except that enamine compound (4-3) was used instead of enamine compound (3-3).

EXAMPLES 37-39

Using a method identical to that in Example 36, photosensitive members independently having the same constitution as Example 36 were prepared by using enamine compounds (4-4), (4-5) and (4-6) respectively in place of enamine compound (4-3) used in Example 36.

With each of the prepared photosensitive members, $V_0$, $E_{\frac{1}{2}}$ and $DDR_5$ were measured by the method identical to that in Example 25.

EXAMPLE 40

An electrophotographic photosensitive member was prepared in the same manner as Example 9, except that enamine compound (4-8) was used instead of enamine compound (1-18).

With the prepared photosensitive member, $V0$, $E_{\frac{1}{2}}$ and $DDR5$ were measured by the method identical to that in Example 25, except that the member was given a corona charge at +6 kV.

EXAMPLES 41-43

Using a method identical to that in Example 40, photosensitive members independently having the same constitution as Example 40 were prepared by using enamine compounds (4-9), (4-11) and (4-13) respectively in place of enamine compound (4-8) used in Example 40.

With each of the prepared photosensitive members, $V0$, $E_{\frac{1}{2}}$ and $DDR5$ were measured by a method identical to that in Example 25.

EXAMPLE 44

Two parts weight disazo pigment represented by the general formula (A), below, one part weight polyester resin (Vylon 200, manufactured by Toyobo Co., Ltd.) and 100 parts weight methyl ethyl ketone were poured into a ball mill pot where they were blended for 24 hours to prepare a photosensitive coating solution. The solution was coated and dried on an aluminum substrate to form a charge generating layer with a thickness of 1μ.

A coating solution prepared by dissolving ten parts weight of the previously mentioned enamine compound (4-14) into solvent, comprising polyallylate resin (U-100, manufactured by Unitika Ltd.) and 100 parts weight chlorobenzene, was coated and dried on the charge generating layer to form a charge transporting layer with a thickness of 15μ. Thus, a photosensitive member was prepared.

With the prepared photosensitive member, $V0$, $E_{\frac{1}{2}}$ and $DDR5$ were measured by a method identical to that in Example 25.

EXAMPLE 45-46

Using the method identical to that in Example 44, photosensitive members independently having the same constitution as Example 44 were prepared by using enamine compounds (4-15) and (4-17) respectively in place of enamine compound (4-14) used in Example 44.

With each of the prepared photosensitive members, $V_0$, $E_{\frac{1}{2}}$ and $DDR_5$ were measured by a method identical to that in Example 25.

The measurement results of $V_0$, $E_{\frac{1}{2}}$ and $DDR_5$ for photosensitive members obtained in Examples 36-46 are shown in Table 4.

TABLE 4

|  | $V_0$ (V) | $E_{\frac{1}{2}}$ (lux·sec) | $DDR_5$ (%) |
| --- | --- | --- | --- |
| Example 36 | −680 | 3.4 | 3.5 |
| Example 37 | −670 | 3.2 | 4.0 |
| Example 38 | −670 | 3.0 | 4.0 |
| Example 39 | −680 | 2.9 | 3.0 |
| Example 40 | +650 | 2.0 | 10.0 |
| Example 41 | +640 | 1.8 | 11.0 |
| Example 42 | +630 | 2.1 | 12.0 |
| Example 43 | +650 | 2.0 | 10.5 |
| Example 44 | −670 | 2.2 | 3.0 |
| Example 45 | −660 | 2.0 | 5.0 |
| Example 46 | −670 | 1.8 | 4.0 |

As can be understood from Table 4, every photosensitive member of the invention, regardless of whether it is a laminated type or single layer type, has a stable initial surface potential of more than 600 V, and excellent charging properties as its dark reduction rate is small enough for the practical use of photosensitive member. The data in the table also show that every photosensitive member of the invention has a high sensitivity. Furthermore, using a commercial electrophotographic copier (EP350Z, manufactured by Minolta Camera Co., Ltd.), copying operation was repeated by giving a positive charge to the photosensitive members, Examples 40 and 41. In 10,000 copying sequences, both the first and final sequences could provide a copied image having excellent gradation. Without any change in sensitivity, high-definition images were obtained throughout the 10,000 copying sequences. Thus, every photosensitive member in the invention has stable repeatability.

EXAMPLE 47

An electrophotographic photosensitive member was prepared in the same manner as Example 5, except that enamine compound (3-29) was used instead of enamine compound (1-9).

With the prepared photosensitive member, $V_0$, $E_{\frac{1}{2}}$ and $DDR_5$ were measured by a method identical to that in Example 1.

EXAMPLE 48

An electrophotographic photosensitive member was prepared in the same manner as Example 9, except that enamine compound (2-33) was used instead of enamine compound (1-18).

With the prepared photosensitive member, $V_0$, $E_{\frac{1}{2}}$ and $DDR_5$ were measured with a method identical to that in Example 1, except that the member was given corona charge at +6 KV.

EXAMPLE 49-50

Using a method identical to that in Example 48, photosensitive member independently having the same constitution as Example 48 were prepared by using enamine compounds (2-30) and (2-31) respectively in place of enamine compound (4-19) used in Example 48.

With each of the prepared photosensitive members, $V_0$, $E_{\frac{1}{2}}$ and $DDR_5$ were measured by a method identical to that in Example 1.

The measuring results of $V_0$, $E_{\frac{1}{2}}$ and $DDR_5$ for photosensitive members of Examples 47-50 are shown in Table 5.

TABLE 5

|  | $V_0$ (V) | $E_{\frac{1}{2}}$ (lux · sec) | $DDR_5$ (%) |
| --- | --- | --- | --- |
| Example 47 | −660 | 3.2 | 5.5 |
| Example 48 | +640 | 1.9 | 10.0 |
| Example 49 | +640 | 1.7 | 11.0 |
| Example 50 | +630 | 1.5 | 12.5 |

As can be understood from Table 5, every photosensitive member of the invention has a stable surface potential of more than 600 V, and excellent charging properties as its dark reduction rate is small enough for the practical use of a photosensitive member. The table also shows that every photosensitive member of the invention has a high sensitivity.

EXAMPLES 51-53

Using a method identical to that in Example 9, photosensitive members independently having the same constitution as Example 9 were prepared by using enamine compounds (2-34), (2-36) and (1-29) respectively in place of enamine compound (1-19) used in Example 9.

With each of the prepared photosensitive members, $V_0$, $E_{\frac{1}{2}}$ and $DDR_5$ were measured by a method identical to that in Example 9.

The measuring results of $V_0$, $E_{\frac{1}{2}}$ and $DDR_5$ for photosensitive members of Examples 51-53 are shown in Table 6.

TABLE 6

|  | $V_0$ (V) | $E_{\frac{1}{2}}$ (lux · sec) | $DDR_5$ (%) |
| --- | --- | --- | --- |
| Example 51 | +630 | 2.6 | 12.0 |
| Example 52 | +630 | 2.3 | 11.5 |
| Example 53 | +620 | 2.8 | 13.0 |

As can be understood from Table 6, every photosensitive member of invention containing enamine compound has, regardless of whether it is a function separating type or dispersion type, an initial surface potential of more than 600 V and excellent charging properties as its dark reduction rate is small enough for the practical use of a photosensitive member. The table also shows that every photosensitive member of the invention has a high sensitivity.

EXAMPLES 54-55

Using a method identical to that in Example 5, photosensitive members independently having the same constitution as Example 5 were prepared by using enamine compounds (3-32) and (2-37) respectively in place of enamine compound (1-19) used in Example 5.

With each of the prepared photosensitive members, $V_0$, $E_{\frac{1}{2}}$ and $DDR_5$ were measured by a method identical to that in Example 5.

EXAMPLE 56

An electrophotographic photosensitive member was prepared in the same manner as Example 33, except that enamine compound (3-34) was used instead of enamine compound (3-18).

With the prepared photosensitive member, $V_0$, $E_{\frac{1}{2}}$ and $DDR_5$ were measured by a method identical to that in Example 25.

EXAMPLE 57

Using a method identical to that in Example 56, a photosensitive member independently having the same constitution as Example 56 was prepared by using the enamine compounds (4-23) in place of enamine compound (3-34) used in Example 56.

With the prepared photosensitive member, $V_0$, $E_{\frac{1}{2}}$ and $DDR_5$ were measured by a method identical to that in Example 1.

The measurement results of $V_0$, $E_{\frac{1}{2}}$ and $DDR_5$ for photosensitive members of Examples 54-57 are shown in Table 7.

TABLE 7

|  | $V_0$ (V) | $E_{\frac{1}{2}}$ (lux · sec) | $DDR_5$ (%) |
| --- | --- | --- | --- |
| Example 54 | +640 | 2.3 | 11.0 |
| Example 55 | +630 | 2.0 | 13.0 |
| Example 56 | −670 | 1.8 | 4.0 |
| Example 57 | −670 | 1.6 | 5.0 |

As can be understood from Table 7, every photosensitive member of the invention has a stable $V_0$ of more than 600 V, and excellent charging properties as its dark reduction rate is small enough for the practical use of a photosensitive member. The table also shows that every photosensitive member of the invention has a smaller $E_{\frac{1}{2}}$, 1.6-2.6 lux.sec, a high sensitivity. Furthermore, using an electrophotographic copier (EP350Z, manufactured by Minolta Camera Co., Ltd.), copying operation was repeated by giving a positive charge to the photosensitive member, Example 54. In 10,000 copying sequences, both the first and final sequences could provide a copied image having excellent gradation. Without any change in sensitivity, high-definition images were obtained throughout the 10,000 copying sequences. Thus, every photosensitive member of the invention has stable repeatability.

COMPARATIVE EXAMPLES 1-8

Photosensitive members were produced in the same manner as in Example 9 excepting that the following eight enamine compounds (a)-(h) were used instead of the enamine compounds (1-18).

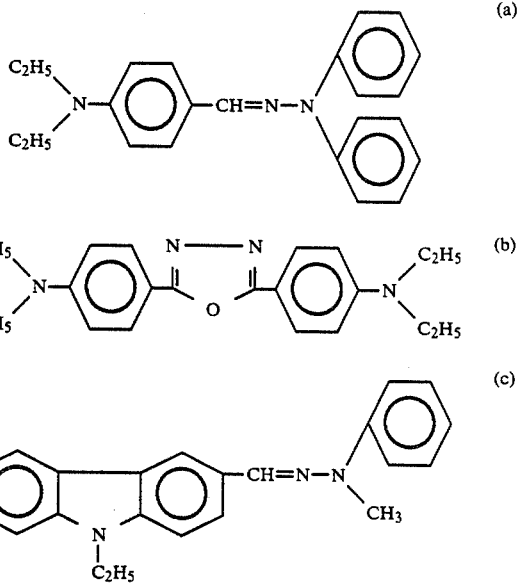

-continued (d) 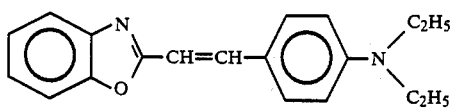

(e) 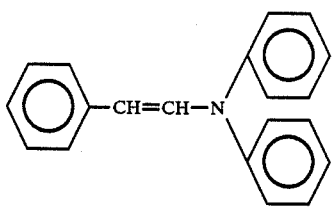

(f) 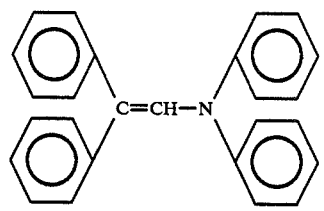

(g) 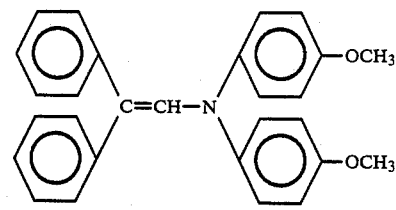

(h) 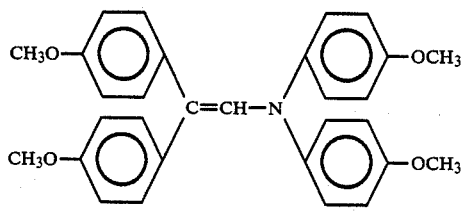

With the prepared photosensitive member, $V_0$, $E_{\frac{1}{2}}$, and $DDR_5$ were measured with the method identical to that in Example 9. The results are shown in Table 8.

TABLE 8

| Comparative Example | enamine compound | $V_0$ (V) | $E_{\frac{1}{2}}$ (lux·sec) | $DDR_5$ (%) |
|---|---|---|---|---|
| 1 | (a) | +640 | 2.8 | 18.0 |
| 2 | (b) | +660 | 32.7 | 6.5 |
| 3 | (c) | +650 | 3.1 | 15.0 |
| 4 | (d) | +660 | 5.8 | 13.0 |
| 5 | (e) | +650 | 39.4 | 5.0 |
| 6 | (f) | +660 | 8.9 | 11.0 |
| 7 | (g) | +660 | 6.3 | 12.5 |
| 8 | (h) | +630 | 2.4 | 20.0 |

On the surface of the photosensitive members of the Comparative Examples 2, 4 and 8, the crystals of the used enamine compounds were separated, and many white spots were observed on the printed image.

What is claimed is:

1. A photosensitive member having a photosensitive layer containing a charge generator and an enamine compound represented by the general formula (I) as a charge transporting material;

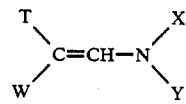

wherein, X and Y independently represents alkyl group, aryl group, aralkyl group, condensed polycyclic group, or heterocyclic group, each of which may have a substituent, providing that at least one of X and Y is a condensed polycyclic group, heterocyclic group, alkyl aryl group, di-substituted aminoaryl group or group represented by a formula:

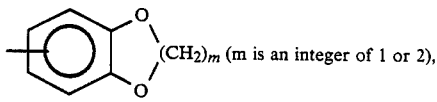

and T and W independently represent hydrogen, an alkyl group, aryl group, aralkyl group, condensed polycyclic group and heterocyclic group, each of which except for hydrogen may have a substituent, except that the both T and W are not hydrogen.

2. The photosensitive member as claimed in claim 1 wherein the aryl group represented by T or W is selected from the group consisting of phenyl group, $C_1$-$C_4$ alkoxy phenyl group, $C_1$-$C_3$ alkyl di-substituted aminophenyl group, a group represented by the formula:

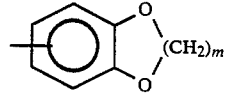

(m is 1 or 2) or a halogenated phenyl group.

3. The photosensitive member as claimed in claim 1 wherein X and/or Y is a condensed polycyclic group which may have a substituent, and T and/or W is selected from the group consisting of phenyl group, $C_1$-$C_4$ alkyl phenyl group, $C_1$-$C_4$ alkoxy phenyl group, $C_1$-$C_3$ alkyl di-substituted or cyclic aminophenyl group, a group represented by the formula:

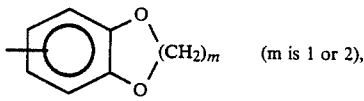

heterocyclic group, halogenated phenyl group condensed polycyclic group or hydrogen.

4. The photosensitive member as claimed in claim 1 wherein X and/or Y is a heterocyclic group which may have a substituent, and T and/or W is selected from the group consisting of phenyl group, $C_1$-$C_4$ alkyl phenyl group, $C_1$-$C_4$ alkoxy phenyl group, $C_1$-$C_3$ alkyl di-substituted or cyclic aminophenyl group or halogenated phenyl group.

5. The photosensitive member as claimed in claim 1 wherein X and/or Y is an alkyl aryl group which may have a substituent, and T and/or W is selected from the group consisting of phenyl group, $C_1$-$C_4$ alkyl phenyl group, $C_1$-$C_4$ alkoxy phenyl group, $C_1$-$C_3$ alkyl di-substituted or cyclic aminophenyl group, a group represented by the formula:

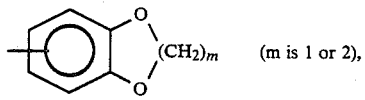 (m is 1 or 2), heterocyclic group, condensed polycyclic group, a halogenated phenyl group or hydrogen.

6. The photosensitive member as claimed in claim 1 wherein X and/or Y is a di-substituted aminoaryl group which may have a substituent, and T and/or W is selected from the group consisting of phenyl group, $C_1$-$C_4$ alkyl phenyl group, $C_1$-$C_4$ alkoxy phenyl group, $C_1$-$C_3$ alkyl di-substituted or cyclic aminophenyl group or condensed polycyclic group.

7. The photosensitive member as claimed in claim 1 wherein X and/or Y is a group represented by the formula:

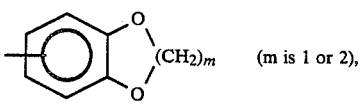 (m is 1 or 2), which may have a substituent, and T and/or W is selected from the group consisting of phenyl group, $C_1$-$C_4$ alkyl phenyl group, $C_1$-$C_4$ alkoxy phenyl group, $C_1$-$C_3$ alkyl di-substituted or cyclic aminophenyl group or condensed polycyclic group.

8. The photosensitive member as claimed in claim 1 wherein the condensed polycyclic group represented by X and/or Y is selected from the group consisting of naphthyl group, alkoxy naphthyl group, alkyl naphthyl group, di-substituted aminonaphthyl group, anthryl or fluorenyl group.

9. The photosensitive member as claimed in claim 1 wherein the heterocyclic group represented by X and/or Y is selected from the group consisting of pyridyl group, pyrrolyl group, purinyl group, carbazolyl group, indolyl group, thienyl group, furyl group, quinolyl group, phenothiazinyl group, indolinyl group, tetrahydroquinolyl group, thiophenyl group, 2,3-dihydrobenzofuryl group, dihydrobenzopyryl group, benzothiazolyl group, benzooxazolyl group, benzoimidazolyl group, thiazolyl group or dibenzofuryl group.

10. The photosensitive member as claimed in claim 1 wherein the alkyl substituted aryl group represented by X and/or Y is an $C_1$-$C_4$ alkylphenyl group.

11. The photosensitive member as claimed in claim 1 wherein the di-substituted aminoaryl group represented by X is a phenyl group having a di-substituted amino group which is selected from the group consisting of di($C_1$-$C_4$ alkyl) amino group, morpholinyl group, piperidyl group, piperazinyl group, 2,3-dihydropyridyl group, tetrahydroquinolyl group, group.

12. The photosensitive member as claimed in claim 1 wherein the enamine compound is a compound represented by the following formula:

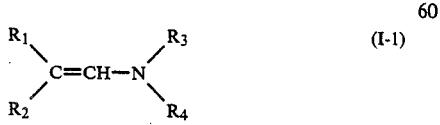 (I-1)

wherein $R_1$ represents hydrogen, alkyl group, aralkyl group, aryl group, condensed polycyclic group and heterocyclic group, each of which except for hydrogen may have a substituent; $R_2$ is aryl group, condensed polycyclic group or heterocyclic group, each of which may have a substituent; $R_3$ is any of a condensed polycyclic group or heterocyclic group, each of which may have substituent; and $R_4$ represents alkyl group, aryl group, aralkyl group, condensed polycyclic group or heterocyclic group, each of which may have a substituent.

13. The photosensitive member as claimed in claim 1 wherein the enamine compound is a compound represented by the general formula;

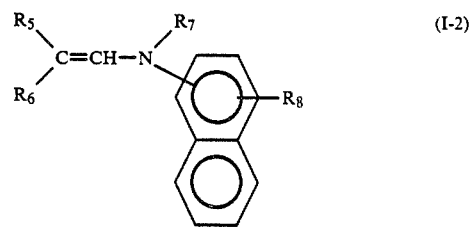 (I-2)

wherein, $R_5$ and $R_6$ independently are hydrogen, aryl group or heterocyclic group, each of which except for hydrogen may have a substituent ($R_5$ and $R_6$ cannnot be simultaneously hydrogen atoms), $R_7$ is an aryl group which may have a substituent, and $R_8$ is hydrogen, alkyl group, alkoxy group or di-substituted amino group.

14. The photosensitive member as claimed in claim 1 wherein the enamine compound is a compound represented by the general formula:

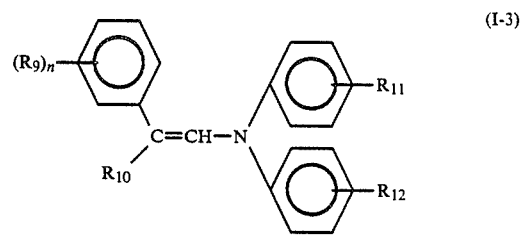 (I-3)

wherein, $R_9$ is hydrogen, alkyl group, alkoxy group, phenoxy group, aralkyloxy group or di-substituted amino group, $R_{10}$ is hydrogen, aryl group or heterocyclic group, each of which except for hydrogen may have a substituent, $R_{11}$ is an alkyl group, $R_{12}$ is hydrogen, alkyl group, alkoxy group or di-substituted amino group, and n is an integer of 1-3.

15. The photosensitive member as claimed in claim 1 wherein the enamine compound is a compound represented by the general formula:

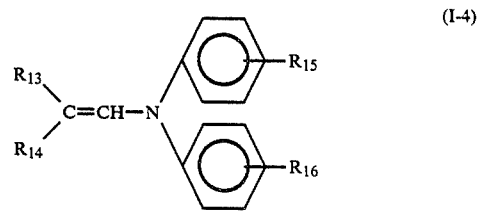 (I-4)

wherein $R_{13}$ is hydrogen, alkyl group or aryl group which except for hydrogen may have a substituent, $R_{14}$ is an aryl group or heterocyclic group, each of which may have a substituent, $R_{15}$ is a di-substituted amino group, and $R_{16}$ is hydrogen, alkyl group, alkoxy group, phenoxy group, aralkyloxy group or di-substituted amino group.

16. The photosensitive member as claimed in claim 1 wherein the enamine compound is a compound represented by the general formula:

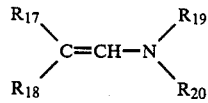     (I-5)

(wherein $R_{17}$ is hydrogen, alkyl group or aryl group which except for hydrogen may have a substituent, $R_{18}$ is an aryl group or heterocyclic group, each of which may have a substituent, $R_{19}$ is a group represented by the formula:

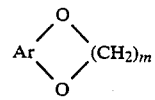

(Ar is a phenyl group, naphtyl group, anthryl group or fluorenyl group; and m is 1 or 2), and $R_{20}$ is hydrogen, alkyl group, alkoxy group, phenoxy group, aralkyloxy group, di-substituted amino group or a group represented by the formula:

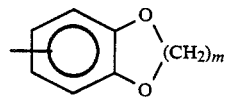

and m is an integer of 1 or 2.

* * * * *